(12) United States Patent
Stern et al.

(10) Patent No.: US 6,891,081 B1
(45) Date of Patent: May 10, 2005

(54) TRANSGENIC MICE OVER-EXPRESSING AMYLOID-BETA ALCOHOL DEHYDROGENASE (ABAD) IN BRAIN AS MODEL OF ALZHEIMER'S DISEASE AND USES THEREOF

(75) Inventors: David M. Stern, Great Neck, NY (US); Shi Du Yan, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/638,695

(22) Filed: Aug. 14, 2000

(51) Int. Cl.⁷ .................... A01K 67/00; A01K 67/027; G01N 33/00; C12N 15/00; C12N 5/00
(52) U.S. Cl. .................... 800/12; 800/3; 800/8; 800/9; 800/13; 800/18; 435/455; 435/463; 435/320.1; 435/325
(58) Field of Search .................... 800/3, 8, 9, 13, 800/12, 18, 21, 22, 25; 435/455, 463, 320.1, 325

(56) References Cited

PUBLICATIONS

Kappel et.al.; Regulating gene expression in transgenic animals, 1992, Current Opinion in Biotechnology 3: 548–553.*
Mullins et.al.; Transgenesis in Normurine Species, 1993, Hypertension vol. 22, No. 4: 630–633.*
Houdebine; Production of pharmaceutical proteins from transgenic animals, 1994, Journal of Biotechnology 34: 269–287.*
Wall; Transgenic Livestock: Progress and Prospects for the Future, 1996, Theriogen.*
Mullins et.al.; Perspectives Series: Molecular Medicine in Genetically Engineered Animals, 1996, J. Clin. Invest., vol. 98: S37–S40.*
Cameron; Recent Advances in Transgenic Technology, 1997, Molecular Biotechnology, vol. 7: 253–265.*
Sigmund; Viewpoint: Are Studies in Genetically Altered Mice Out of control?, 2000, Arterioscler Thromb Vasc. Biol. 20: 1425–1429.*
Chapman et.al.; Transgenic farm animals get off the ground, 1998, Transgenic Research 7: 73–75.*
Moechars et.al.; Early Phenotypic Changes in Transgenic Mice . . . of Amyloid Precursor Protein in Brain, 1999, Journal of Biological Chemistry, vol. 274: 6483–6492.*
Ying He et.al.; Brain L–3 Hydroxyacyl–coenzyme a Dehydrogenase Is Identical . . . in Alzheimer's Disease, 1998, Journal of Biological chemistry, vol. 273: 10741–10746.*
Akama TK, et al.: Amyloid β–peptide stimulates nitric oxide production in astrocytes through an NFkB–dependent mechanism. Proc.Natl. Acad. Sci. (1998) 95 :5795–5800; (Exhibit 1).

Combs, Colin K, et al.: Identification of Microglial Signal Transduction Pathways Mediating a Neurotoxic Response to Amyloidogenic Fragments of β–Amyloid and Prion Proteins. Journal of Neuroscience. (1999) 19 (3): 928–939; (Exhibit 2).
Hardy J,:The Alzheimer family of disease: Many etiologies, one pathogenesis?. Proc. Natl. Acad. Sci (1997):2095–2097; (Exhibit 3).
He X–Y, Merz G, Mehta P, Schulz H, Yang S–Y: Human brain short chain L–3–hydroxyacyl Coenzyme A dehydrogenase is a single–domain multifunctional enzyme. *J Biol Chem* (1999); 274: 15014–15019; (Exhibit 4).
He X–Y, Schulz H, Yang S–Y: A human brain L–3–hydroxyacyl coenzyme A dehydrogenase is identical to amyloid beta–peptide–binding protein involved in Alzheimer's disease. *J Biol Chem* 1998; 273: 10741–10746; (Exhibit 5).
Hsia A, Masliah E, McConlogue L, Yu G–Q, Tatsuno G, Hu K, Kholodenko D, Malenka R, Nicoll R, Mucke L: Plaque–independent disruption of neural circuits in Allzheimer's disease mouse models. Proc. Natl. Acad. Sci. (1999) 96:3228–3233; (Exhibit 6).
Hsiao K, Chapman P, Nilsen S, Eckman C, Harigaya Y, Younkin S, Yang F, Cole G,: Correlative Memory Deficits, Aβ Elevation, and Amyloid Plaques in Transgenic Mice. Science. (1996) 99–102; (Exhibit 7).
Picciotto M., Wickman K.: Using Knockout and Transgenic Mice to study Neurophysiology and Behavior. American Physiological Society. (1998) 1131–1163; (Exhibit 9).
Schenk D, Barnour R, Dunn W, et al. : Immunization with amyloid –β attenuates alzheimer–disease–like pathology in the PDAPP mouse. Nature. (1999) 173–177; (Exhibit 10).
Yan SD, et al.: An intracellular protein that binds amyloid–β peptide and mediates neurotoxicity in Alzheimer's disease. Nature. (1997)389: 689–1017; (Exhibit 11).
Yan SD, Zhu H, et al.: Receptor –dependent cell stress and amyloid accumulation in systemic amyloidosis. Nature Medicine. (2000) 6: 643–651. (Exhibit 12).

* cited by examiner

*Primary Examiner*—Deborah Crouch
*Assistant Examiner*—Thaian N. Ton
(74) *Attorney, Agent, or Firm*—John P. White; Cooper & Dunham LLP

(57) ABSTRACT

The present invention provides for a transgenic non–human animal whose cells contain a recombinant DNA sequence comprising a nerve tissue specific promoter operatively linked to a DNA sequence which encodes amyloid-beta peptide alcohol dehydrogenase (ABAD), and exhibits at least one phenotype from the group consisting of: overexpression of ABAD, elevated levels of basal ATP; protection from metabolic or ischemic stress.

8 Claims, 13 Drawing Sheets

PD-huABAD construct (5.8)

PD-hu ABAD transgenic cassette (3.1 kb)

FIGURE 4A   FIGURE 4B   FIGURE 4C   FIGURE 4D
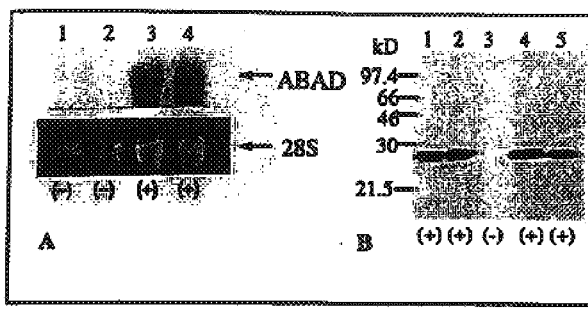
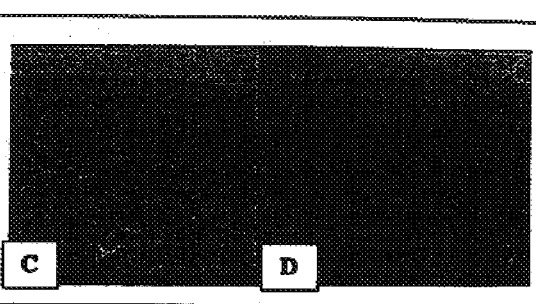

Figure 7A-D
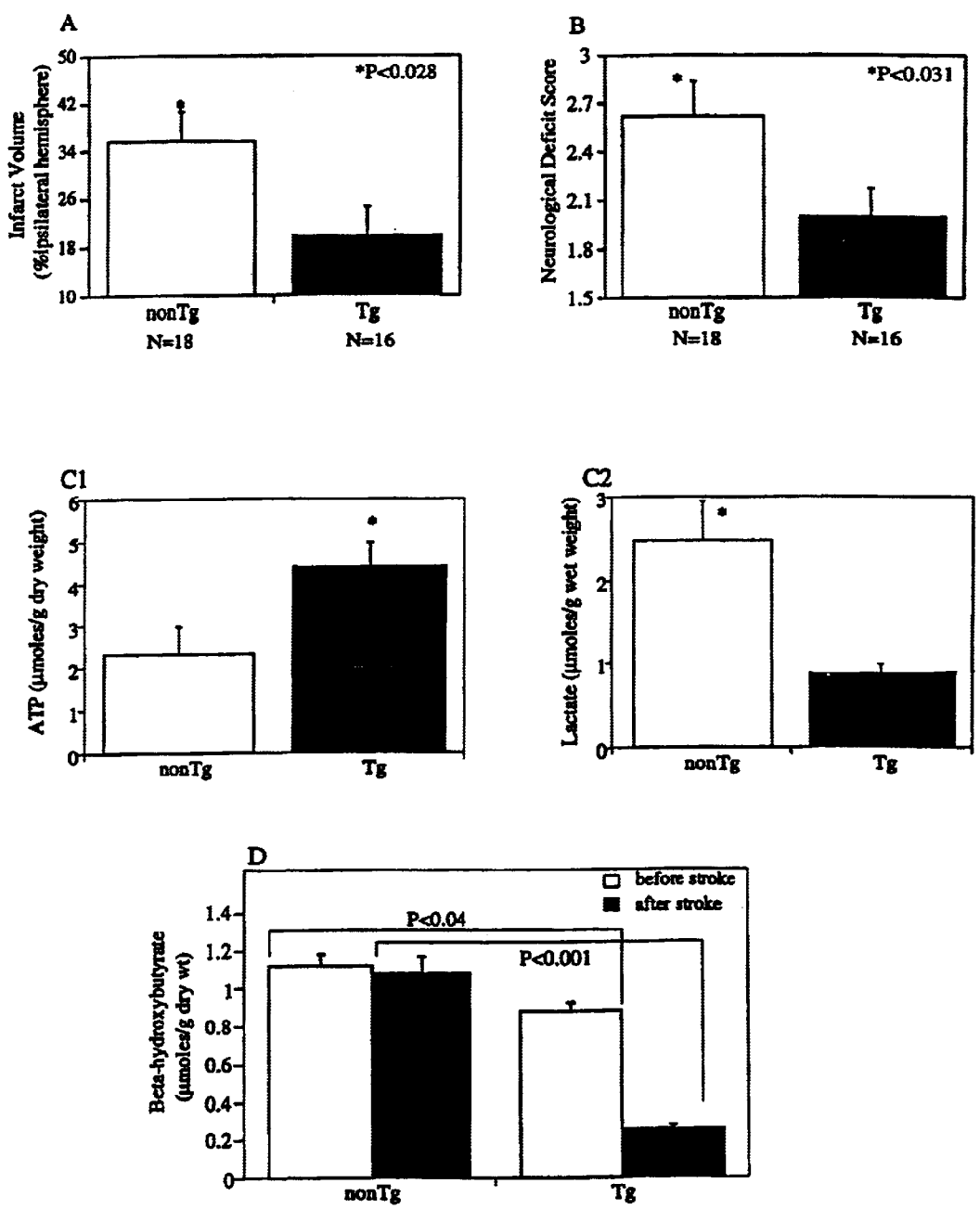

*FIGURE 10A*          *FIGURE 10B*
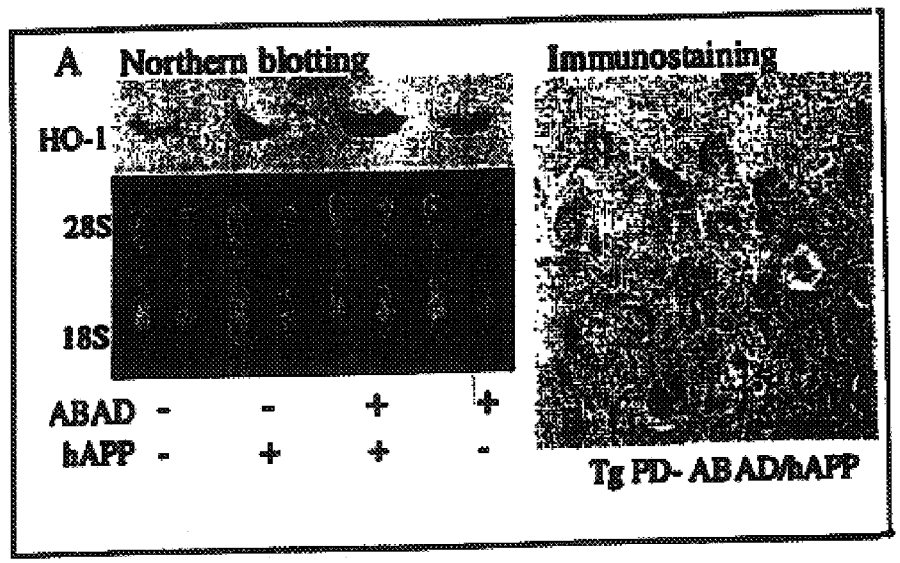
*FIGURE 10C*    *FIGURE 10D*    *FIGURE 10E*
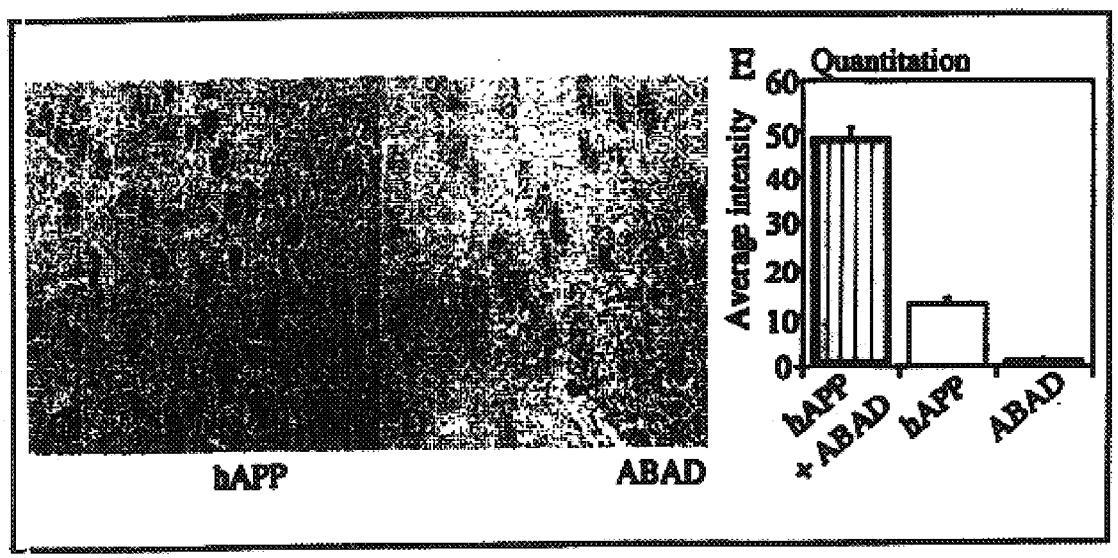

TRANSGENIC MICE OVER-EXPRESSING AMYLOID-BETA ALCOHOL DEHYDROGENASE (ABAD) IN BRAIN AS MODEL OF ALZHEIMER'S DISEASE AND USES THEREOF

The invention disclosed herein was made with Government support under Grant No.AG16736 from the National Institute on Aging in the National Institutes of Health of the U.S. Department of Public Health. Accordingly, the U.S. Government has certain rights in this invention.

BACKGROUND OF THE INVENTION

Throughout this application, various publications are referenced by number. Full citations for these publications may be found listed at the end of the specification immediately preceding the claims. The disclosures of these publications in their entireties are hereby incorporated by reference into this application in order to more fully describe the state of the art as known to those skilled therein as of the date of the invention described and claimed herein.

The pain of Alzheimer's disease results directly from the memory loss and cognitive deficits suffered by the patient. These eventually result in the patient's loss of identity, autonomy, and freedom. As a step toward curing this disease, alleviating its symptoms, or retarding its progression, it would be desirable to develop a transgenic animal model exhibiting the main debilitating phenotype of Alzheimer's disease, that is, memory loss, expressed concomitantly with the neuropathological correlates of Alzheimer's disease, for example, beta-amyloid accumulation, increased glial reactivity, and hippocampal cell loss.

It is estimated that over 5% of the U.S. population over 65 and over 15% of the U.S. population over 85 are beset with some form of Alzheimer's disease (Cross, A. J., Eur J Pharmacol (1982) 82:77–80; Terry, R. D., et al., Ann Neurol (1983) 14:497506). It is believed that the principal cause for confinement of the elderly in long term care facilities is due to this disease, and approximately 65% of those dying in skilled nursing facilities suffer from it.

Certain facts about the biochemical and metabolic phenomena associated with the presence of Alzheimer's disease are known. Two morphological and histopathological changes noted in Alzheimer's disease brains are neurofibrillary tangles (NFT) and amyloid deposits. Intraneuronal neurofibrillary tangles are present in other degenerative diseases as well, but the presence of amyloid deposits both in the interneuronal spaces (neuritic plaques) and in the surrounding microvasculature (vascular plaques) seems to be characteristic of Alzheimer's. Of these, the neuritic plaques seem to be the most prevalent (Price, D. L., et al., Drug Development Research (1985) 5:59–68). Plaques are also seen in the brains of aged Down's Syndrome patients who develop Alzheimer's disease.

SUMMARY OF THE INVENTION

The present invention provides for a transgenic non-human animal whose cells contain a recombinant DNA sequence comprising a nerve tissue specific promoter operatively linked to a DNA sequence which encodes amyloid-beta peptide alcohol dehydrogenase (ABAD), wherein said non-human animal exhibits at least one phenotype from the group consisting of: overexpression of ABAD, elevated levels of basal ATP; protection from metabolic or ischemic stress.

BRIEF DESCRIPTION OF THE FIGURES

FIG. 1A: entire construct; FIG. 1B: transgenic cassette for microinjection.

FIGS. 4A, 4B, 4C and 4D. ABAD expression in Tg PD-ABAD mice (+) compared with nontransgenic littermate controls (–). FIG. 4A (Northern) and FIG. 4B (Western) analysis of homogenates of cerebral cortex. Equal amounts of RNA (note approximately equal intensity of 28S ribosomal RNA band on the ethidium bromide stained gel) and protein were loaded in each lane. FIGS. 4C–4D show immunohistochemical identification of ABAD in cerebral cortex from a Tg PD-ABAD mouse (FIG. 4C) and a nontransgenic littermate control (FIG. 4D).

FIG. 6A. The spectrum from a representative Tg PD-ABAD mouse displays prominent glutamate and glutamine peaks. The inset shows expanded regions of resonances of glutamate (G-4), glutamine (GL-4) and GABA (GA-2) from Tg (PD-ABAD) mice. Abbreviations: G-2, G-3, and G-4 denote the position 2, 3, and 4 carbons of glutamate, respectively; GL-2, GL-3 and GL-4 denote the position 2, 3 and 4 carbons of glutamine, respectively; and, GA-2 corresponds to C-2 of GABA. FIG. 6B. The effect of ABAD overexpression on areas of glutamate C-4 resonance in brain extracts of Tg PD-ABAD and nonTg littermate control mice as obtained from $^{13}$C-NMR analysis. Values are expressed as the ratio of the area of the glutamate C-4 peak over the area of an added standard acetate (see Methods). *Glutamate and glutamine levels were significantly higher in Tg PD-ABAD mice than in nonTg controls (P<0.03; N=4, in each case). Total areas of $^{13}$C-glutamate (G-2+G-3+G-4) were significantly higher in the Tg PD-ABAD compared with nonTG littermate controls. FIG. 6C. Basal ATP levels in whole brain extracts from Tg PD-ABAD (N=5) or nonTg littermate controls (N=5) were measured as described in the text. Animals were fasted overnight, and the brain was removed and freeze-clamped for ATP and β-hydroxybutyrate (BHB) analysis. * indicates P>0.03. In each case, the data is reported as the mean±SD.

FIGS. 7A–7D. Induction of stroke in Tg PD-ABAD mice. FIGS. 7A–7B. Tg PD-ABAD mice and nonTg littermates were subjected to middle cerebral artery occlusion and were evaluated 24 hrs after the ischemic insult to determine neurologic deficit score (FIG. 7B), and, following sacrifice, infarct volume (FIG. 7A). FIGS. 7C–7D. At the same time point, cerebral cortex was harvested to determine ATP (FIG. 7C1), lactate (FIG. 7C2) and β-hydroxybutyrate (BHB) (FIG. 7D) levels determined on extracts of whole brains (from animals subjected to the stroke procedure 24 hrs previously) from Tg PD-ABAD or nonTg control mice (N=5, in each case). Data is reported as the mean±SD (P<0.04 for ATP and P<0.03 for lactate). Transient middle cerebral artery occlusion model of stroke in mice: comparison of infarct volume in Tg PD-ABAD and nontransgenic littermate controls (nonTg). P<0.05.

FIGS. 9A–9D demonstrate immunocytochemistry of representative sections and the far right panel (FIG. 9E) shows quantitation of immunocytochemical results from multiple fields of all mice in each of the experimental groups.

FIGS. 10A–10E. Increased expression of heme oxygenase (HO)-1 in cerebral cortex from double Tg mice overexpressing ABAD and mutant human APP (hAPP). FIG. 10A, Northern analysis for HO-1 transcripts. FIGS. 10B–10D, immunostaining for HO-1 antigen. FIG. 10E, Quantitation of immunocytochemical results from multiple fields of all mice in each of the experimental groups.

FIGS. 12A1, 12A2, 12A3, 12A4, and 12B. Increased expression of activated caspase-3 in cerebral cortex from Tg PD-ABAD/hAPP mice. FIGS. 12A1–12A4, immunostaining for activated caspase-3. FIG. 12B, quantitation of immunocytochemical results from multiple fields of all mice in each of the experimental groups. Scale bar, 10 µm.

DETAILED DESCRIPTION OF THE INVENTION

Figure 1A:
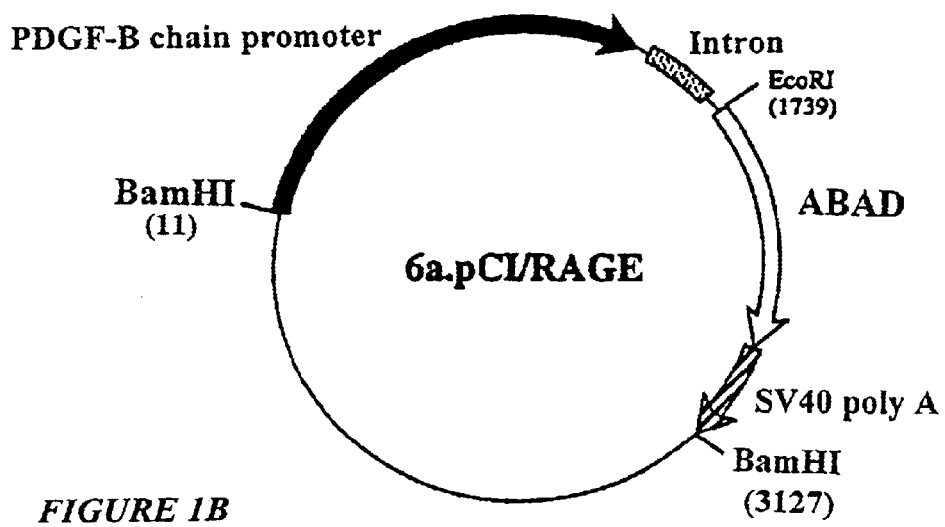
FIGS. 1A–1B. Schematic depiction of strategy for making Tg PD-ABAD mice.

The present invention provides for a transgenic non-human animal whose cells contain a recombinant DNA sequence comprising a nerve tissue specific promoter operatively linked to a DNA sequence which encodes amyloid-beta peptide alcohol dehydrogenase (ABAD), wherein said non-human animal exhibits at least one phenotype from the group consisting of: overexpression of ABAD, elevated levels of basal ATP; protection from metabolic or ischemic stress.

The present invention also provides for a method for evaluating in a non-human transgenic animal the potential therapeutic effect of an agent or compound for treating Alzheimer's disease in a human, which comprises: (a) providing an agent to a transgenic non-human animal whose cells comprise a recombinant DNA sequence comprising a nerve tissue specific promoter operatively linked to a DNA sequence which encodes amyloid-beta peptide alcohol dehydrogenase (ABAD), (b) determining the therapeutic effect of the agent or compound on the transgenic non-human animal by monitoring basal synaptic transmission or synaptic plasticity, wherein an increase in basal synaptic transmission or synaptic plasticity indicates that the agent would have a potential therapeutic effect on Alzheimer's disease in a human.

As used herein, agent and compound are used interchangeably.

In one embodiment of the invention, the promoter of both element (a) and (b) is platelet derived growth factor (PDGF)-B-chain promoter.

In another embodiment of the invention, the non-human animal is a mouse, a rat, a sheep, a dog, a primate, or a reptile.

In another embodiment, the animal is a mammal.

The invention provides for a transgenic mouse whose cells contain a recombinant DNA sequence comprising:(a) a nerve tissue specific promoter; and (b) a DNA sequence which encodes amyloid-beta peptide alcohol dehydrogenase (ABAD), wherein the promoter and the DNA sequence which encodes amyloid-beta peptide alcohol dehyrdogenase are operatively linked to each other and integrated in the genome of the mouse, and wherein said mouse exhibits at least one phenotype from the group consisting of: increased ATP level in cerebral cortex; decreased lactate level in cerebral cortex and lower beta-hydroxybutyrate levels in cerebral cortex which has been subjected to cerebral ischemia.

In one embodiment of the invention, the recombinant DNA sequence consists essentially of a nerve tissue specific promoter operatively linked to a DNA sequence which encodes amyloid-beta peptide alcohol dehydrogenase (ABAD).

In another embodiment of the invention, the recombinant DNA sequence consists of a nerve tissue specific promoter operatively linked to a DNA sequence which encodes amyloid-beta peptide alcohol dehydrogenase (ABAD).

In one embodiment of the invention, the DNA sequence which encodes amyloid-beta peptide alcohol dehydrogenase is a human DNA sequence.

The present invention also provides for a method for increasing the resistance of a cell to metabolic stress which comprises introducing into the cell a recombinant DNA molecule which comprises a promoter operatively linked to a DNA sequence encoding amyloid beta alcohol dehydrogenase (ABAD) wherein the cell expresses ABAD, thereby increasing the basal level of ATP in the cell and increasing the resistance of the cell to metabolic stress.

In one embodiment of the invention, the metabolic stress is ischemia, nutritional stress or excitotoxic stress. In another embodiment of the invention, the cell is a human pancreatic islet cell.

The sequences for ABAD are publically available in the GenBank. For example, several sequences of ABAD obtained from the GenBank are recited below:

LOCUS HCD2_RAT 261 aa ROD 30 May 2000
DEFINITION 3-HYDROXYACYL-COA DEHYDROGENASE TYPE II (TYPE II HADH) (ENDOPLASMIC RETICULUM-ASSOCIATED AMYLOID BETA-PEPTIDE BINDING PROTEIN).
ACCESSION O70351PID g7387724
VERSION O70351 GI:7387724DB
SOURCE swissprot: locus HCD2_RAT, accession 070351; class: standard. created: May 30, 2000, sequence updated: May 30, 2000, annotation updated: May 30, 2000, xrefs: gi: 2961552, gi: 2961553 xrefs (non-sequence databases): HSSP P19992, PFAM PF00106, PROSITE PS00061KEYWORDS Oxidoreductase; NAD; Acetylation.
SOURCE Norway rat. ORGANISM *Rattus norvegicus* Eukaryota; Metazoa; Chordata; Craniata; Vertebrata; Euteleostomi; Mammalia; Eutheria; Rodentia; Sciurognathi; Muridae; Murinae; Rattus.
REFERENCE 1 (residues 1 to 261)
AUTHORS Gunn-Moore, F. J. and Tavare, J. M. TITLE Direct Submission
JOURNAL Submitted (??-FEB-1998) to the EMBL/GenBank/DDBJ databases

REMARK SEQUENCE FROM N.A. TISSUE=LIVERCOMMENT

[CATALYTIC ACTIVITY] L-3-HYDROXYACYL-COA+NAD(+)=3-OXOACYL-COA+NADH.

[SUBUNIT] TETRAMER (BY SIMILARITY).

[SUBCELLULAR LOCATION] MITOCHONDRIAL (BY SIMILARITY).

[SIMILARITY] BELONGS TO THE SHORT-CHAIN DEHYDROGENASES/REDUCTASES (SDR) FAMILY.FEATURES Location/Qualifiers source 1..261/organism="Rattus norvegicus"/db_xref="taxon:10116" 1..261 Protein 1..261/product="3-HYDROXYACYL-COA DEHYDROGENASE TYPE II"/EC_number="1.1.1.35" Site 2/site_type="acetylation"/note="(BY SIMILARITY)." Site 12..37/site type="np-binding"/note="NAD (BY SIMILARITY)." Site 168/site_type="active"/note="BY SIMILARITY."

Origin 1 maaavrsvkg lvavitggas glglstakrl vgqgatavll dvpnsegete akklggncif 61 apanvtseke vqaaltlake kfgridvavn cagiavaikt yhekknqvht ledfqrvinv 121 nligtfnvir lvagvmgqne pdqggqrgvi intasvaafe gqvgqaaysa skggivgmt l 181 piardlapig irvvtiapgl fatpllttlp dkvrnflasq vpfpsrlgdp aeyahlvqmv 241 ienpflngev irldgairmq p// (SEQ ID NO:1)

LOCUS AF035555 973 bp mRNA PRI 07-MAY-1998

DEFINITION Homo sapiens short chain L-3-hydroxyacyl-CoA dehydrogenase (SCHAD) mRNA, complete cds.

ACCESSION AF035555

VERSION AF035555.1 GI:3116433

KEYWORDS

.SOURCE human.

ORGANISM Homo sapiens Eukaryota; Metazoa; Chordata; Craniata; S Vertebrata; Euteleostomi; Mammalia; Eutheria; Primates; Catarrhini; Hominidae; Homo.

Referecne 1 (bases 1 to 973)

AUTHORS He, X. Y., Schulz, H. and Yang, S. Y.

TITLE A human brain L-3-hydroxyacyl-coenzyme A dehydrogenase is identical to an amyloid beta-peptide-binding protein involved in Alzheimer's disease JOURNAL J. Biol. Chem. 273 (17), 10741–10746 (1998)

MEDLINE 98221216

REFERENCE 2 (bases 1 to 973)

AUTHORS Yang, S.-Y., Schulz, H. and He, X.-Y.

TITLE Direct Submission

JOURNAL Submitted (21 Nov. 1997) Pharmacology, Institute for Basic Research in Developmental Disabilities, 1050 Forest Hill Road, Staten Island, N.Y. 10314, USAFEATURES Location/Qualifiers source 1..973/organism="Homo sapiens"/db_xref="taxon:9606"/chromosome="X"/map="Xpll.21"/cell type="neuron"/tissue type="brain" gene 1..973/gene="SCHAD" CDS 25..810/gene="SCHAD"/EC_number="1.1.1.35"/note="fatty acid beta-oxidation enzyme"/codon_start=1/product="short chain L-3-hydroxyacyl-CoA dehydrogenase"/protein_id="AAC15902.1"/db_xref="GI:3116434"/translation="MAAACRSVKGLVAVITGGASGLGLA-TAERLVGQGASAVLLDLPN
SGGEAQAKKLGNNCVFAPADVTSEKD-VQTALALAKGKFGRVDVAVNCAGIAVASKTYN LKKGQTHTLEDFQRVLDVNLMGTFN-VIRLVAGEMGQNEPDQGGQRGVIINTASVAAFE GQVGQAAYSASKGGIVGMTLPIARD-LAPIGIRVMTIAPGLFGTPLLTSLPEKVCNFLA SQVPFPSRLGDPAEYAHLVQAIIENP-FLNGEVIRLDGAIRMQP (SEQ ID NO:2)

BASE COUNT 222 a 262 c 287 g 202 t

Origin 1 tcccgtggag tggccggcga caagatggca gcagcgtgtc ggagcgt-gaa gggcctggtg 61 gcggtaataa ccggaggagc ctcgggcctg ggcctggcca cggcggagcg acttgtgggg 121 cagggagcct ctgctgtgct tctggacctg cccaactcgg gtggggaggc ccaagc-caag 181 aagttaggaa acaactgcgt tttcgcccca gccgacgtga cctctgagaa ggatgtgcaa 241 acagctctgg ctctagcaaa aggaaagttt ggccgtgtgg atgtagctgt caactgtgca 301 ggcatcgcgg tggctagcaa gacgtacaac ttaaagaagg gccagac-cca taccttggaa 361 gacttccagc gagttcttga tgtgaatctc atgggcacct tcaatgtgat ccgcctggtg 421 gctggtgaga tgggc-cagaa tgaaccagac cagggaggcc aacgtgggt catcatcaac 481 actgccagtg tggctgcctt cgagggtcag gttggacaag ctg-catactc tgcttccaag 541 gggggaatag tgggcatgac actgc-ccatt gctcgggatc tggctcccat aggtatccgg 601 gtgatgacca ttgccccagg tctgtttggc accccactgc tgaccagcct cccagagaaa 661 gtgtgcaact tcttggccag ccaagtgccc ttccctagcc gactgggtga ccctgctgag 721 tatgctcacc tcgtacaggc cat-catcgag aacccattcc tcaatggaga ggtcatccgg 781 ctg-gatgggg ccattcgtat gcagccttga agggagaagg cagagaaaac acacgctcct 841 ctgcccttcc tttccctggg gtactactct ccagtct-tgg gaggaagccc agtagccatt 901 ttgtaactgc ctaccagtcg ccctctgtgc ctaataaagt ctctttttct cacagaaaaa 961 aaaaaaaaaa aaa// (SEQ ID NO:3)

Definitions

"DNA sequence" is a linear sequence comprised of any combination of the four DNA monomers, i.e., nucleotides of adenine, guanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organisms natural phenotype.

"zygote" is a diploid cell having the potential for development into a complete organism. The zygote can result from parthenogenesis, nuclear transplantation, the merger of two gametes by artificial or natural fertilization or any other method which creates a diploid cell having the potential for development into a complete organism. The origin of the zygote can be from either the plant or animal kingdom.

In the practice of any of the methods of the invention or preparation of any of the pharmaceutical compositions an "therapeutically effective amount" is an amount which is capable of alleviating the symptoms of the disorder of memory or learning in the subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

By "nervous system-specific" is meant that expression of a nucleic acid sequence occurs substantially in a nervous system tissue (for example, the brain or spinal cord). Preferably, the expression of the nucleic acid sequence in the nervous system tissue represents at least a 5-fold, more preferably, a 10-fold, and, most preferably, a 100-fold increase over expression in non-nervous system tissue.

The "non-human animals" of the invention include vertebrates such as rodents, non-human primates, sheep, dog, cow, amphibians, reptiles, etc. Preferred non-human animals are selected from the rodent family including rat and mouse, most preferably mouse.

The "transgenic non-human animals" of the invention are produced by introducing "transgenes" into the germline of the non-human animal.

Advantages of the Present Invention

The transgenic non-human mammals of the present invention will provide insights with respect to how and where protein interactions occur in Alzheimer's Disease and thus provide more useful models for testing the efficacy of certain drugs in preventing or reducing the onset or progression of this disease. The transgenic non-human mammals of the present invention include recombinant genetic material comprised of a nucleic acid sequence encoding ABAD fused to specific promoters capable of expressing the protein in specific tissues such as nerve tissues generally and/or specific types of nerve tissue, e.g., the brain.

As described herein, the current invention provides a number of advantages. First, because transgenic animals are generally useful for the investigation of specific biological processes and for reproducing particular aspects of human disease, the transgenic animals of the invention provide an important, reproducible and accurate means for screening drugs to isolate therapeutic agents. In particular, the transgenic animals that are described for the first time herein have the advantage of mimicking the cognitive defects observed in patients with Alzheimer's disease. Accordingly, the efficacy of a particular therapy may be examined in the same animal at different disease stages. Importantly, because this invention provides a transgenic animal model of Alzheimer's disease with measurable phenotypes, compounds may be screened to identify those which alleviate this symptom, even absent knowledge of the symptom's underlying biological cause.

In addition, although not strictly required for drug screening, the associated neuro-pathological symptoms exhibited by the transgenic animal models described herein provide the unique advantage of allowing the investigation of the etiology of Alzheimer's disease. For example, the appearance of reduced synaptic plasticity or the reduced basal synaptic transmission may be correlated with the appearance of specific behavioral impairments within individuals or groups of animals. In addition, treatments which are shown to improve memory function may be tested for their ability to selectively improve certain pathological symptoms.

Another advantage of this invention is the ease with which these transgenic animals are bred to produce identical transgenic progeny. The animals of the invention may be generated in sufficient quantity to make them widely and rapidly available to researchers in this field.

The ABAD single transgenic exhibited phenotypes which were unexpected. It was unexpected that basal ATP levels would be elevated and that the animals would be protected from metabolic (ischemic) stress. This is an important point, since it suggests that gene therapy (to increase ABAD levels) or other means to induce ABAD gene expression (expression of the enzyme) could have a protective effect.

The following procedure is carried out: Introduction of ABAD into neurons or other cells (we did this also in cultured COS cells as described hereinbelow in the Examples), increases their resistance to metabolic stress as represented by an ischemic microenvironment, excitotoxic stress or nutritional stress (decreased glucose). We have recently obtained data that shows in a kainate model of brain injury, neuronal loss is less in these ABAD transgenic mice.

In addition, the ABAD gene has been introduced into pancreatic islet cells in order to see if it would enhance their viability after transplantation. In this case, survival means that few islet cells would be needed for a particular transplant recipient for the tranplant to be successful and accordingly, the surviving islet cells being able to produce insulin. This is of great value to patients who are islet transplant recipients since the problem in islet cell transplantation is that there are too few islet cells available and if the number of islet cells per transplant were reduced, then the number of transplants possible would increase. Therefore, it is clear that one property exhibited by the ABAD overexpressing transgenic and by the islet cells which have ABAD expressed via introduction of a recombinant expression construct (DNA including a sequence encoding ABAD operatively linked to a promoter sequence and integrated into the genome of the islet cells) is that of cytoprotection. This cytoprotection is due, at least in part, to the consequence that overexpression of ABAD (as shown in the phenotype of the ABAD transgenic) results in an increase in cellular ATP.

Further Detailed Description of the Invention

The present invention also provides for a transgenic nonhuman animal whose germ or somatic cells contain a nucleic acid molecule which comprises a nerve tissue specific promoter operatively linked to a DNA sequence which encodes amyloid-beta peptide alcohol dehydrogenase (ABAD), introduced into the mammal, or an ancestor thereof, at an embryonic stage.

This transgenic animal may be used in screening methods for compounds which would be useful in the treatment of neurological disorders in humans. A method for screening compounds for their potential use as therapeutic agents which comprises administering to the transgenic non-human mammal described herein the compound, in various amounts, and observing whether the neurological function of the transgenic mammal improves or not (as determined by, for example, basal synaptic transmission, synaptic plasticity, neuronal stress, et al.).

The neurological disorder may be amnesia, Alzheimer's disease, amyotrophic lateral sclerosis, a brain injury, cerebral senility, chronic peripheral neuropathy, a cognitive disability, a degenerative disorder associated with learning, Down's Syndrome, dyslexia, electric shock induced amnesia or amnesia. Guillain-Barre syndrome, head trauma, Huntington's disease, a learning disability, a memory deficiency, memory loss, a mental illness, mental retardation, memory or cognitive dysfunction, multi-infarct dementia and senile dementia, myasthenia gravis, a neuromuscular disorder, Parkinson's disease, Pick's disease, a reduction in spatial memory retention, senility, or Turret's syndrome.

The compound which is tested in the screening method of the present invention may be an organic compound, a nucleic acid, a small molecule, an inorganic compound, a lipid, or a synthetic compound. The mammal may be a mouse, a sheep, a bovine, a canine, a porcine, or a primate. The administration may comprise intralesional, intraperitoneal, intramuscular or intravenous injection; infusion; liposome-mediated delivery; gene bombardment; topical, nasal, oral, anal, ocular or otic delivery.

The present invention also provides for a method for alleviating symptoms in a subject suffering from a neurological disorder which comprises administering to the subject an effective amount of the compound evaluated by the methods hereinabove in an amount effective to treat the symptoms in the subject suffering from a neurological disorder.

The administration may be intralesional, intraperitoneal, intramuscular or intravenous injection; infusion; liposome-mediated delivery; gene bombardment; topical, nasal, oral, anal, ocular or otic delivery.

Pharmaceutical Compositions and Carriers

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with 125I or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment the compound of the present invention is associated with a pharmaceutical carrier which includes a pharmaceutical composition. The pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

Transaenic Technology and Methods

The following U.S. Patents are hereby incorporated by reference: U.S. Pat. No. 6,025,539, IL-5 transgenic mouse; U.S. Pat. No. 6,023,010, Transgenic non-human animals depleted in a mature lymphocytic cell-type; U.S. Pat. No. 6,018,098, In vivo and in vitro model of cutaneous photoaging; U.S. Pat. No. 6,018,097, Transgenic mice expressing human insulin; U.S. Pat. No. 6,008,434, Growth differentiation factor-11 transgenic mice; U.S. Pat. No. 6,002,066; H2-M modified transgenic mice; U.S. Pat. No. 5,994,618, Growth differentiation factor-8 transgenic mice; U.S. Pat. No. 5,986,171, Method for examining neurovirulence of polio virus, U.S. Pat. No. 5,981,830, Knockout mice and their progeny with a disrupted hepsin gene; U.S. Pat. No. 5,981,829, DELTA.Nur77 transgenic mouse; U.S. Pat. No. 5,936,138; Gene encoding mutant L3T4 protein which facilitates HIV infection and transgenic mouse expressing such protein; U.S. Pat. No. 5,912,411, Mice transgenic for a tetracycline-inducible transcriptional activator; U.S. Pat. No. 5,894,078, Transgenic mouse expressing C-100 app.

The methods used for generating transgenic mice are well known to one of skill in the art. For example, one may use the manual entitled "Manipulating the Mouse Embryo" by Brigid Hogan et al. (Ed. Cold Spring Harbor Laboratory) 1986.

See for example, Leder and Stewart, U.S. Pat. No. 4,736,866 for methods for the production of a transgenic mouse.

For sometime it has been known that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases by either gene therapy or by using a transgenic non-human mammal as a model system of a human disease. This model system can be used to test putative drugs for their potential therapeutic value in humans.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism can be used for the in vivo analysis of the gene expression, which expression is believed to be related to a particular genetic disease.

Attempts have been made to study a number of different types of genetic diseases utilizing such transgenic animals. Attempts related to studying Alzheimer's disease are disclosed within published PCT application WO89/06689 and PCT application WO89/06693, both published on Jul. 27, 1989, which published applications are incorporated herein by reference to disclose genetic sequences coding for Alzheimer's .beta.-amyloid protein and the incorporation of such sequences into the genome of transgenic animals.

Embryonal target cells at various developmental stages can be used to introduce transgenes. Different methods are used depending on the stage of development of the embryonal target cell. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al. (1985) Proc. Natl. Acad. Sci. U.S.A. 82, 4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci U.S.A. 73, 1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al. (1985) Proc. Natl. Acad. Sci. U.S.A. 82, 6927–6931; Van der Putten, et al. (1985) Proc. Natl. Acad. Sci U.S.A. 82, 6148–6152). Transfection is easily and efficiently obtained by culturing the blastomeres on a monolayer of virus-producing cells (Van der Putten, supra; Stewart, et al. (1987) EMBO J. 6, 383–388). Alternatively, infection can be performed at a later stage. Virus or virus-producing cells can be injected into the blastocoele (Jahner, D., et al. (1982) Nature 298, 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra).

A third type of target cell for transgene introduction is the embryonal stem cell (ES). ES cells are obtained from pre-implantation embryos cultured in vitro and fused with embryos (Evans, M. J., et al. (1981) Nature 292, 154–156; Bradley, M. O., et al. (1984) Nature 309, 255–258; Gossler, et al. (1986) Proc. Natl. Acad. Sci U.S.A. 83, 9065–9069; and Robertson, et al. (1986) Nature 322, 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468–1474.

As used herein, a "transgene" is a DNA sequence introduced into the germline of a non-human animal by way of human intervention such as by way of the above described methods.

The disclosures of publications referenced in this application in their entireties are hereby incorporated by reference into this application in order to more fully describe the state of the art as known to those skilled therein as of the date of the invention described and claimed in herein.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Generation of Transgenic Mice With Targeted Overexpression of Amyloid-beta Peptide Alcohol Dehydrogenase (ABAD) in Neurons This section describes a means of making transgenic mice with targeted overexpression of ABAD in neurons using the PDGF B-chain promoter and the cDNA for human full-length ABAD. The mice, termed "Tg PD-ABAD," which have been produced provide a model system for determining the consequences of heightened ABAD expression in neurons, and could serve as an important model system to test ABAD inhibitors. Cross-breeding of Tg PD-ABAD mice with other animals, such as those expressing a transgene causing overexpression of mutant amyloid precursor protein (resulting in increased production of amyloid-beta peptide) provide a model system to assess the effects of ABAD in an Aβ-rich environment in the brain relevant to Alzheimer's disease. In addition, isolation and culture of embryonic neurons from Tg PD-ABAD mice allows study of the consequences of increased levels of ABAD in vitro in actual neurons. These are several examples of how Tg PD-ABAD mice can be used to assess the contribution of ABAD, analyzed according to in vitro and in vivo systems, to situations potentially relevant to human disease.

Introduction

Amyloid-beta peptide alcohol dehydrogenase (ABAD) is a member of the short-chain dehydrogenase reductase family of oxidoreductases[1-6]. ABAD is present in endoplasmic reticulum and mitochondrial[1,3]. It shares in common with other members of the family cofactor binding sites (in this case for NAD[H]) and a Rossman fold. However, it appears to be unique in its ability to bind amyloid-beta peptide (Aβ) and to utilize a range of substrates, including hydroxyacyl Coenzyme A adducts, β-hydroxybutyrate, alcohols and steroids (17β-estradiol etc)[2,4-6]. Possible physiologic roles for ABAD are suggested by the lethal phenotype observed on inactivation of scully, the Drosophila counterpart, which is associated with multiple developmental abnormalities[7]. However, in an Aβ-rich environment, ABAD appears to switch from a physiologic to a pathogenic role. In cultured cell systems, overexpression of ABAD appears to confer increased sensitivity to the toxic effects of Aβ[1,2]. For example, COS or neuroblastoma cells overexpressing APP (V717G) when cotransfected to overexpress ABAD display exaggerated cell stress based on generation of reactive aldehydes (malondialdehyde and 4-hydroxynonenal; HNE), and increased DNA fragmentation[2]. Taken together with the increased levels of ABAD in neurons in the brains of patients with Alzheimer's disease (AD), this has led us to speculate that ABAD might be an important cofactor for Aβ-induced cell stress. Furthermore, from its location in the endoplasmic reticulum it could potentially interact with nascent Aβ allowing it to participate in pathogenesis at early times.

This section demonstrates the production of mice overexpressing ABAD in neurons under control of the PDGF B-chain promoter. The resulting transgenic mice have several evident uses: 1) a model for demonstrating the consequences of increased ABAD expression in neurons (as in response to ischemic stress, though this could be extended to inflammatory and other stimuli); 2) a model for testing the effect of inhibitors of ABAD (at the level of the enzyme's active site, determinants mediating interaction with Aβ, or other critical portions of the molecule); 3) a source of cultures for primary cortical neurons overexpressing ABAD (which could be used to test inhibitors); and, 4) a starting point for cross-breeding studies to produce double-transgenic mice (for example, cross-breeding with mice overexpressing the hAPP transgene which results in increased generation of Aβ; the double transgenic mice resulting from such a cross display increased levels of ABAD in an Aβ-rich environment).

Methods

Figure 1B:
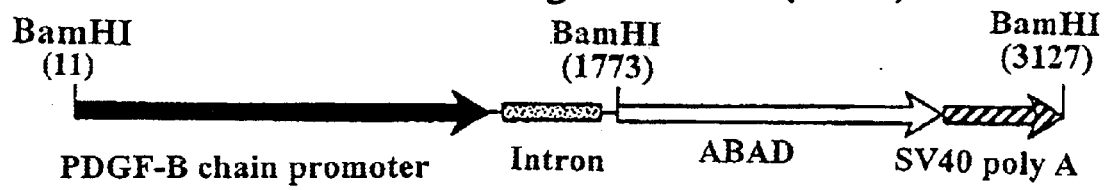

Construction of the transgene and making the transgenic (Tg) mice. The platelet-derived growth factor (PDGF) B-chain promoter was used to drive overexpression of ABAD in neurons of the central nervous system of transgenic (Tg) mice[8]. Transgene constructs were prepared using a previously described vector[9,10]. Briefly, the CMV immediate/early promoter was excised from the commercial expression vector pCI (Promega, Madison Wis.), and replaced with an oligonucleotide polylinker. The PDGF B-chain promoter fragment was mobilized as an Xba1 fragment[8] and cloned into a unique Spel site designed within the synthetic linker. The full-length human ABAD cDNA was inserted into the NotI site of the original polylinker. A schematic representation of this construct is shown in FIG. 1A. An ~3 kb fragment containing the promoter, cDNA and required other sequences was then excised from the plasmid backbone as a PvuI fragment (FIG. 1B) and microinjected mouse B6CBAF$_1$/J oocytes. The latter were implanted into pseudopregnant females and mated with B6CBAF$_1$/J males resulting in the generation of independent founders. Breeding of these mice demonstrated germ-line transmission and was used to produce lines of animals termed Tg PD-ABAD.

Founders were initially identified by Southern blotting performed on DNA extracted from mouse tails. DNA was digested, run on agarose gels, and hybridized with $^{32}$P-labelled cDNA for human ABAD. Tails were digested with proteinase K (500 µg/ml) in digestion buffer (50 mM Tris, pH 8.0, 100 mM EDTA, 0.5% SDS) at 55° C. for overnight. Then, purified DNA was cleaved with EcoRI overnight at 37° C. Labelling of the probe was done using the Stratagene's Probe Labeling Kit™. Autoradiography was then performed.

Subsequent screening of progeny was by PCR using the following primers: 5'-GGCAGCAGCGTGTCGGAGCG-3' (SEQ ID NO:4) and 3'-AGGGCAGAGGAGCGTGTGT-5' (SEQ ID NO:5). Total RNA was isolated using Trizol®, and RT-PCR was performed with the following thermocycling parameters: 30 sec for each cycle consisting of incubations at 95° C. for 20 sec, 57° C. for 30 sec and 72° C. for 1 sec for a total of 35 cycles. Products were analyzed by agarose gel electrophoresis (1%) and visualized by ethidium bromide staining under ultraviolet illumination. The size of the ABAD amplicon with these primers corresponded to 821 bp.

Northern and immunoblotting utilized the same procedures as above, except that tissue was homogenized in the presence of Trizol (RNA) or in homogenization buffer (Tris/HCl, 10 mM, pH 7.4; NaCl, 100 mM; phenylmethylsulfonylfluoride, 100 µg/ml; EDTA, 1 mM; aprotonin, 1 µg/ml). Note that immunoblotting and immunostaining of brain tissue from Tg PD-ABAD mice used anti-human ABAD peptide IgG which appears to be preferentially immunoreactive with human ABAD, the latter encoded by the transgene.

Characterization of ABAD expression in Tg PD-ABAD mice. Northern analysis was performed on total RNA isolated from cerebral cortex, hippocampus and cerebellum. RNA was isolated using Trizol® followed by electrophoresis on 0.8% agarose gels (30 µg was applied to each lane), transfer to nitrocellulose membranes, and hybridization with $^{32}$P-labelled human ABAD cDNA. The ABAD cDNA was labelled by as above.

Western blotting was performed on protein extracts of brain subregions. Proteins were extracted from minced pieces of brains by exposing the tissue to lysis buffer (Tris/HCl, 20 mM; pH 7.4; Triton X-100, 1%; phenylmethylsulfonylfluoride, 2 mM; EDTA, 1 mM, aprotonin, 10 µg/ml; leupeptin, 10 µg/ml) using a ratio of 1 ml of buffer per 0.5 gm of tissue. Extracts were then boiled in reducing SDS-sample buffer, and applied to SDS-PAGE (12%) according to Laemmli[11]. Antibody to recombinant human ABAD was employed as described[2].

Immunostaining was performed on paraformaldehyde (4%)-fixed, paraffin embedded sections (6 µm) of mouse brains prepared according to standard methods[12,13]. The sections were deparaffinized and dehydrated, and then stained with rabbit anti-human ABAD IgG (50 µg/ml) followed by goat anti-rabbit biotin-conjugated IgG and ExtrAvidin-conjugated with alkaline phosphatase (Biotin ExtrAvidin® kit; Sigma, St. Louis Mo.). Preparation of anti-ABAD IgG, using recombinant ABAD as the immunogen, has been described[2].

Cross-breeding of Tg PD-ABAD mice with hAPP mice. Tg mice overexpressing an alternatively spliced hAPP minigene that encodes hAPP695, hAPP751, and hAPP770 bearing mutations linked to familial AD (V717F, K670M/N671L) have been produced by Dr. Lennart Mucke[14], and provided to us for use in cross-breeding studies with Tg PD-ABAD mice. In these mice, expression of the transgene is also driven by the PDGF B-chain promoter. cross-breeding was performed and double-transgenic mice expressing both hAPP and PD-ABAD transgenes were identified with specific primers. The primers for the hAPP transgene were: 5'-GACAAGTATCTCGAGACACCTGGGGATGAG-3' (SEQ ID NO:6) and 3'-AAAGAACTTGTAGGTTGGATTTTCGTACC-5' (SEQ ID NO:7). PCR conditions for the amplifying the hAPP transgene were the same as those described above, and the size of the amplicon was 1169 bp.

Characterization of Tg PD-ABAD/hAPP mice. Mice were anesthetized according to standard procedures and then flush-perfused transcardially with solution containing NaCl (0.9%). Brains will then be rapidly removed and divided sagitally. One hemibrain was postfixed in phosphate-buffered saline (PBS) containing paraformaldehyde (4%; pH 7.4) at 4° C. for 48 hrs prior to vibratome sectioning. Hemibrains were stored in cryoprotectant medium (phosphate-buffered saline containing glycerin and ethylene glycol) until sectioning. This portion of the brain was employed for studies of neuronal integrity and degeneration. There is ample evidence that loss of synaptophysin-immunoreactivity in presynaptic terminals is associated with AD brain, a marker which correlates with extent of cognitive impairments[15-20]. Additionally, immunoreactivity for Microtubule-associated protein (MAP)-2 was examined as a marker of neuronal cell bodies and dendrites, as a significant decrease of MAP-2 immunoreactive dendrites has been observed for example, in brains of patients with neurodegeneration subsequent to HIV-1 encephalitis[21].

Hemibrains were subjected to sagittal sectioning employing a Leica Vibratome 1000E. Sections, 40 µm thick, were prepared and collected into the wells of 12-well tissue culture plates in cryoprotectant medium and stored at -20° C. until immunostaining was performed. Two sections per mouse were randomly selected for further study, based on full integrity of the sample, i.e., clearly delineated neocortex, and CA1, CA2 and CA3 were completely intact. Prior to immunohistochemistry, free-floating sections were placed individually in wells of 24-well tissue culture plates and washed twice in phosphate-buffered saline (PBS; pH 7.4; containing calcium/magnesium). Sections were then permeabilized in PBS containing Triton X-100® (0.2%) for 20 min at room temperature. Sections were stained with antibodies to perform assessment of neuronal integrity. Anti-synaptophysin IgG (Boehringer) was employed as a marker of presynaptic terminals. Anti-MAP-2 IgG (Boehringer) was employed as a marker of neuronal cell bodies/dendrites. The appropriate nonimmune IgG was employed as a control (Boehringer Mannheim). After appropriate blocking steps, primary antibodies were incubated with sections and then washed in PBS. FITC-labeled secondary antibodies (Vector system; ABC) were employed to visualize sites of primary antibody binding. After washing, sections were mounted using Vectashield® on glass slides and then coverslips placed atop the sections. Sections will then be kept in the dark at 4° C., for no more than two weeks prior to analysis.

Semiquantitative evaluation of neuronal integrity was performed using laser scanning confocal microscopy. Neuronal integrity was assessed in the neocortex and pyramidal cell layer of the hippocampus (CA1 subfield) in six sections per mouse (two for each antibody marker). For each mouse, 4–8 confocal images (3–4/section) of the neocortex, and 2–4 confocal images (1–2/section) of the hippocampal CA1 subfield, each covering an area of 210×140 μm, were obtained. Under 60×, oil immersion, the sample was focused and iris and gain levels adjusted to obtain images with a pixel intensity within a linear range. Each final image was processed sequentially in Lasersharp. Digitized images were then transferred to a Macintosh computer using Adobe Photoshop, JPEG compression and analyzed with NIH Image. The area of the neuropil occupied by MAP-2-labeled dendrites or by synaptophysin-labeled presynaptic terminals was quantified and expressed as a percentage of the total image area as described[21]. Final analysis of digitized images for area neuropil occupied was determined by two independent investigators. Mean±standard deviation is reported for each section. Control sections were studied under conditions in which primary antibody was omitted, and no signal was observed with secondary antibody alone.

Immunostaining of mouse brain for other markers employed commercially available goat antibody to murine macrophage-colony stimulating factor (goat anti-M-CSF IgG; 10 μg/ml; Santa Cruz), rabbit antibody to activated caspase 3 (50 μg/ml; PharMingen), and mouse monoclonal antibody to phosphorylated tau (AT8; 10 μg/ml; Immunogenetics). In each case, the immunostaining protocol used standard techniques according to the manufacturer's instructions. Rabbit anti-murine Interleukin (IL) 6 IgG was provided by Dr. Gerald Fuller (University of Alabama Medical Center, Birmingham) and has been used in previous studies[22]. Sections were incubated with primary antibodies overnight at 4° C., followed by blocking with appropriate antisera and addition of biotin-conjugated goat anti-rabbit, goat anti-mouse or mouse anti-goat IgG (1:25 dilution) for 30 min at 37° C. Then ExtrAvidin conjugated to peroxidase or to alkaline phosphatase (1:25 dilution) was added for 25 min at 37° C. Slides were then washed and developed with 3-amino-9-ethyl carbazole or fast red. Sections were viewed in an Olympus microscope, and images were quantified using the Universal imaging system.

Activation of the transcription factor NF-kB was studied in brains of mice and in neurons cultured from this tissue (see below). Nuclear extracts were prepared according to the method of Dignam et al.[23], and were incubated with $^{32}$P-labelled double stranded consensus oligonucleotide probe for NF-kB (Santa Cruz) followed by polyacrylamide gel electrophoresis and autoradiography. These methods have been described previously using brain tissue and cultured cells as the samples for preparation of nuclear extracts[12].

Isolation and characterization of neurons from Tg PD-ABAD mice. Brains of E16–18 mouse embryos were processed by a modification of a previously described method[24]. In brief, Embryos were washed in ethanol (75%), transferred to a dish with sterile phosphate-buffered saline (PBS) at 4° C. under a tissue culture hood. Two embryos were dissected at a time immersed in Neurobasal Medium (GIBCO) with NaCl (22 mM), NaHCO$_3$ (4.4 mM), penicillin (50 units/ml) and streptomycin (50 μg/ml). The embryo tail was removed and analyzed by PCR to determine genotype (as above). Cerebral cortex was dissected free from the cerebellum and brainstem, sliced into 1 mm pieces, and transferred to 1.5 ml eppendorf tubes in the above medium. The tube was centrifuged at 400 rpm, the pellet was washed in PBS, and resuspended in PBS. Then, trypsin (0.25%; 0.5 ml) and DNAse (250 units/ml) were added and the incubation was continued for 15 min at 37° C. with gentle shaking. The mixture was decanted, washed twice in PBS by inverting the tube and gently spinning at 400 rpm for 5 min. Neurons were cultured in growth medium (Neurobasal Medium with B27, 2%, L-glutamine, 2 mM, penicillin, 50 units/ml, streptomycin, 50 μg/ml) in wells coated with poly-L-lysine. Neurons were identified immunocytochemically using antibody to neurofilament (Sigma) and the methods for immunostaining described above.

$^{13}$C-NMR spectroscopy. $^{13}$C NMR spectroscopy is a powerful technique for measuring substrate metabolism in tissue and cell culture[25-31]. Addition to culture supernatant or perfusing organs with D-[2,4-$^{13}$C]-3-hydroxybutyrate results in the [$^{13}$C]-labelling of TCA cycle intermediates from labeled acetyl CoA[29,30]. Although TCA cycle intermediates are usually present at concentrations too low to be observed by NMR spectroscopy, glutamate, which is present at millimolar concentrations, is in rapid exchange with α-ketoglutarate via aminotransferase reactions. Thus, if [$^{13}$C]-labeled acetyl CoA enters the TCA cycle, the $^{13}$C-label will be detectable as [$^{13}$C]-glutamate. For experiments with cultured cells (10$^7$ cells/NMR determination), D-[$^{13}$C]-β-hydroxybutyrate (10 mM) was added to DMEM (without glucose or pyruvate) and dialyzed fetal calf serum (10%). For in vivo studies, D-[$^{13}$C]-β-hydroxybutyrate was infused intravenously as follows over 60 min: 0.75 M [$^{13}$C]-β-hydroxybutyrate administered as a bolus (0.05 ml) followed by a constant infusion with a total volume of 1.5 ml[31]. At the end of the infusion, brain samples were freeze-clamped under liquid nitrogen and stored at −80° C. Frozen tissue (sample size, 92±6 and 88±11 mg, for Tg and nonTg mice, respectively) was extracted with perchloric acid, neutralized with sodium hydroxide as described[28-30], and homogenates were lyophilized and resuspended in D$_2$O for NMR analysis. For cell culture studies, culture supernatants and lysates were extracted with perchloric acid followed by neutralization and lyophilization as above.

High resolution carbon spectra were acquired on a Bruker 500 MHz spectrometer, using a 10 mm broad-band probe tuned to 125.77 MHz. Field homogeneity was optimized by shimming on the D$_2$O lock signal. Spectra were obtained using a 25 KHz sweep width, with 45° pulse and 2 s interpulse delay. Heteronuclear decoupling was performed using a Waltz sequence. Each spectrum represents a total of 17,920 scans. The assignment of $^{13}$C resonances was based on previously published studies[26,27,29-31]. Glutamate peak areas were determined using Bruker NMR software, and are expressed as ratios with the summed area of the [2,4-$^{13}$C] β-hydroxybutyrate peaks. In brain extracts, the area measurements for glutamate, glutamine and γ-amino butyric acid (GABA) are compared with spectra obtained from an external standard solution ([$^{13}$C]-acetate, 0.1 M) using the same acquisition parameters as above. The $^{13}$C NMR spectra of standard solutions of glutamine and GABA were obtained to confirm chemical shifts of these compounds in the brain extracts.

$^1$H NMR Spectroscopy. Water pre-saturation experiments were acquired on the GE500 MHz spectrometer using a 5 mm inverse detection probe ($^1$H observe, with broad band decoupling capabilities). With a sweep width of 5 KHz, a 45° pulse width, and the carrier frequency set on the H$_2$O peak for a 1 s pre-saturation pulse, $^1$H spectra were obtained for 256 total scans. Presaturation experiments were performed both with and without heteronuclear $^{13}$C decoupling (for assessing the fractional enrichment in glutamate), centered at 40 ppm, using a Waltz sequence.

The region between 2.6–2.0 ppm reveals proton resonances from the C-4 of glutamate. Although the proton resonances corresponding to [$^{12}$C-4]glutamate are resolvable, the $^1$H satellites corresponding to [$^{13}$C-4] glutamate are obscured by other nearby peaks. Accordingly, the fractional enrichment of glutamate cannot be determined by measuring the areas of the proton peaks bound to labeled and nonlabeled carbons, as is the case with lactate[25]. However, the enrichment of glutamate C-4 may be determined from the increase in intensity of the C-4 glutamate proton resonances following heteronuclear $^{13}$C-decoupling, as these resolvable resonances then correspond to the sum of protons from labeled and nonlabeled glutamate[25].

Induction of stroke in Ta PD-ABAD mice. Functional consequences of overexpression of ABAD were first assessed in response to ischemic stress, the transient middle cerebral artery occlusion model. Murine stroke model Mice (C57BL6/J, male) were subjected to stroke according to previously published procedures[32]. Following anesthesia, the carotid artery was accessed using the operative approach previously described in detail[33], including division/coagulation of the occipital and pterygopalatine arteries to obtain improved visualization and vascular access. A nylon suture was then introduced into the common carotid artery, and threaded up the internal carotid artery to occlude the origin of the right middle cerebral artery (MCA). Nylon (polyamide) suture material was obtained from United States Surgical Corporation (Norwalk, Conn.), and consisted of 5.0 nylon/13 mm length for 27–36 g mice, and 6.0 nylon/12 mm length for 22–26 g mice. After 45 minutes of occlusion, the suture was withdrawn to achieve a reperfused model of stroke. Although no vessels were tied off after the suture was removed, the external carotid arterial stump was cauterized to prevent frank hemorrhage.

Measurements of relative cerebral blood flow were obtained as previously reported[32-35] using a straight laser doppler flow probe placed 2 mm posterior to the bregma, and 6 mm to each side of midline using a stereotactic micromanipulator, keeping the angle of the probe perpendicular to the cortical surface. These cerebral blood flow measurements, expressed as the ratio of ipsilateral to contralateral blood flow, were obtained at baseline, and immediately prior to MCA occlusion, 45 minutes after MCA occlusion, and at several time points after withdrawal of the occluding suture.

Measurement of Cerebral Infarction Volumes: After 24 hours, animals were euthanized and their brains rapidly harvested. Infarct volumes were determined by staining serial cerebral sections with triphenyl tetrazolium chloride and performing computer-based planimetry of the negatively (infarcted) staining areas to calculate infarct volume (using NIH image software).

Neurological Exam: Prior to giving anesthesia, mice were examined for neurological deficit 23 h after reperfusion using a four-tiered grading system: a score of 1 was given if the animal demonstrated normal spontaneous movements; a score of 2 was given if the animal was noted to be turning towards the ipsilateral side; a score of 3 was given if the animal was observed to spin longitudinally (clockwise when viewed from the tail); and, a score of 4 was given if the animal was unresponsive to noxious stimuli. This scoring system has been previously described in mice[32-34], and is based upon similar scoring systems used in rats[36]. Immunostaining of cerebral cortex following induction of stroke in wild-type mice was performed as described above using a rabbit polyclonal antibody made using purified recombinant murine ABAD as the immunogen. Quantitation of microscopic images was accomplished with the Universal Imaging System.

Results

Figure 2:
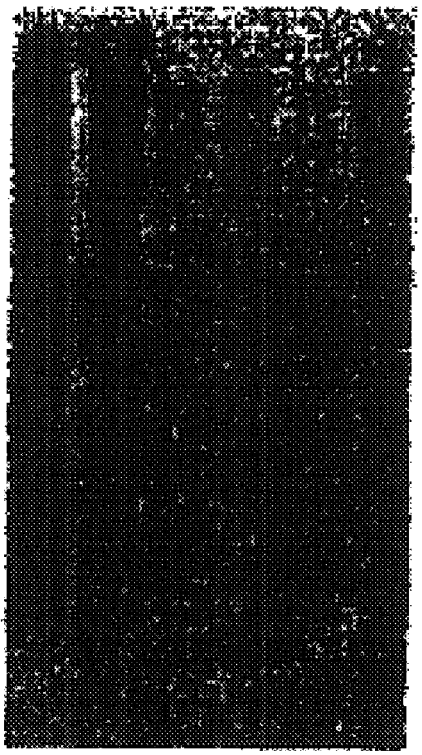
FIG. 2. Southern analysis of three founders for Tg PD-ABAD mice: lanes 1–3 show mice positive for the transgene and lanes 4–6 are nontransgenic littermates.
Figure 3:
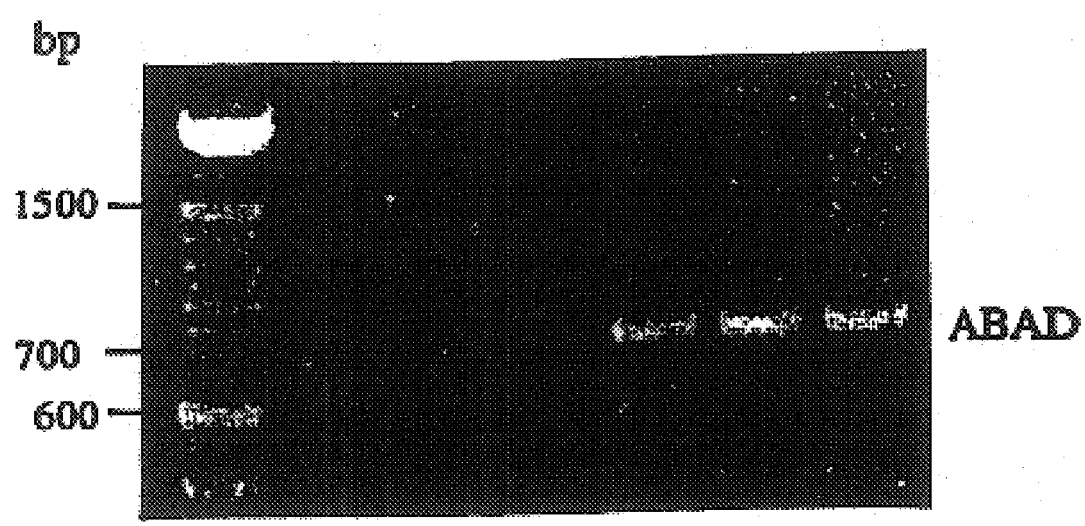
FIG. 3. Identification of Tg PD-ABAD mice (+) and nontransgenic littermate controls (–) by PCR.

Identification of Tg PD-ABAD mice. Southern analysis identifying three Tg PD-ABAD founders is shown in FIG. 2. These mice were used to generate lines of Tg PD-ABAD mice in whom the progeny were identified by PCR using the primers described in the methods section. An example of PCR detection of positive founders, versus negative non-Tg is animals is shown in FIG. 3.

Figure 5:
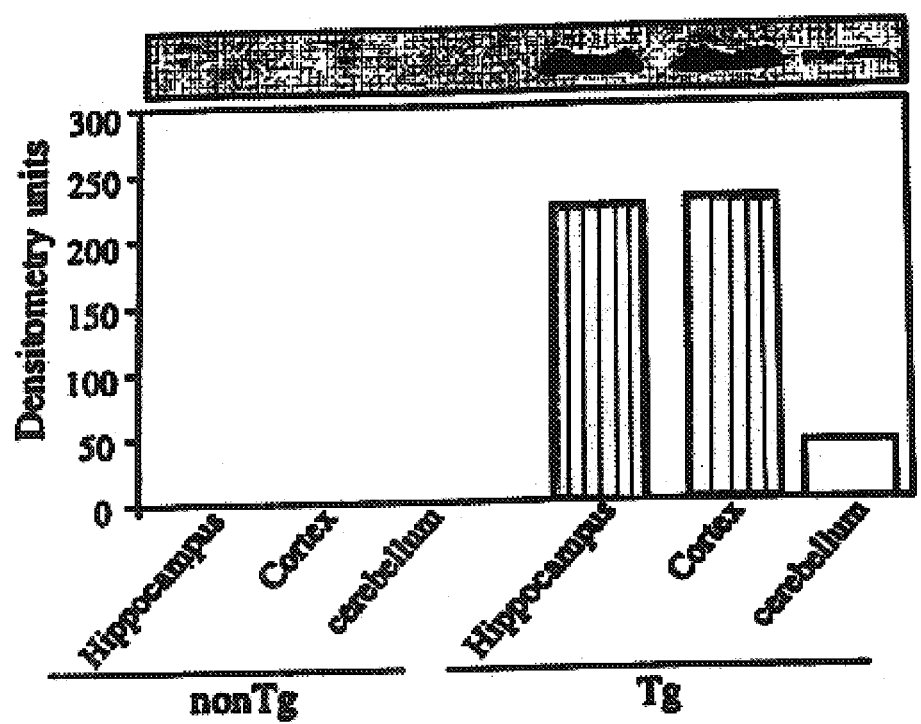
FIG. 5. ABAD expression in brain subregions of Tg PD-ABAD mice compared with nontransgenic littermate controls (nonTg). Immunoblotting was performed protein extracts of brain homogenates derived from the indicated brain subregion.

Characterization of Tg PD-ABAD mice. Expression of the transgene in the brain was determined by Northern analysis of total RNA extracted from cerebral cortex with $^{32}$P-labelled cDNA for human ABAD (FIG. 4A). An intense band was observed in Tg PD-ABAD mice, but not in nontransgenic littermate controls. Similarly Western analysis was performed on protein extracts of cerebral cortex from transgenic mice using antibody to recombinant ABAD expressed in bacteria[2]. Again, a strong band of immunoreactivity migrating just below the 30 kDa molecular weight marker confirmed the presence of high levels of ABAD antigen in brains of Tg PD-ABAD mice compared with nontransgenic littermate controls (FIG. 4B). Immunoblotting was then performed on brain subregions, including cerebral cortex, hippocampus and cerebellum, with anti-ABAD IgG (FIG. 5). In Tg PD-ABAD mice, intense immunoreactive bands were seen in cerebral cortex and hippocampus, compared with lower levels of transgene expression in the cerebellum. Immunostaining with anti-ABAD IgG confirmed that the increased levels of ABAD in Tg PD-ABAD animals were in neurons (FIGS. 4C–D). These data indicate that Tg PD-ABAD mice provide a model system in which neurons of the brain, especially cerebral cortex and hippocampus express high levels of ABAD.

Figure 6A:
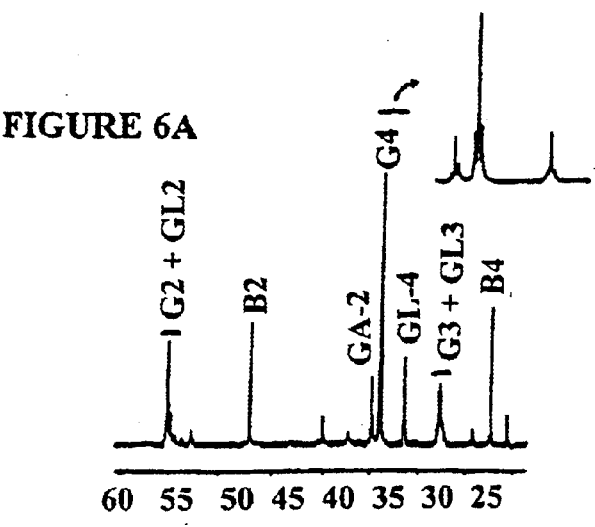
FIGS. 6A–6C. The effect of ABAD overexpression on the proton-decoupled 13C NMR spectra of freeze-clamped brain after perfusion with D-[2,4-$^{13}$C]β-hydroxybutyrate.
Figure 6B:
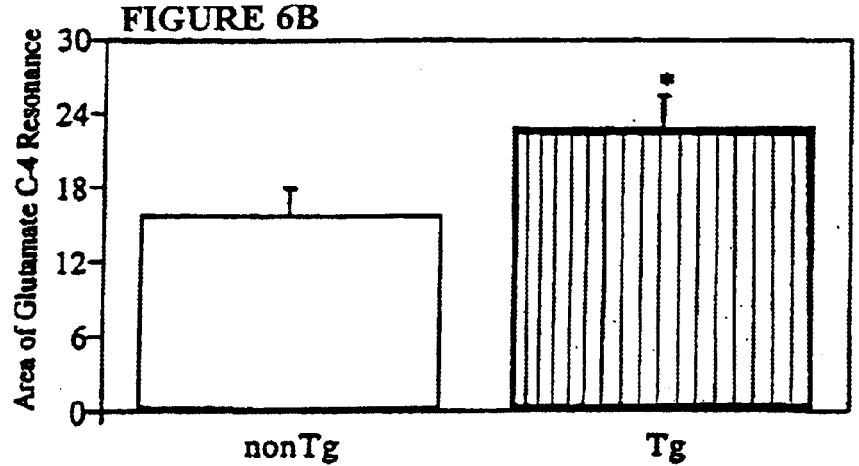
Figure 6C:
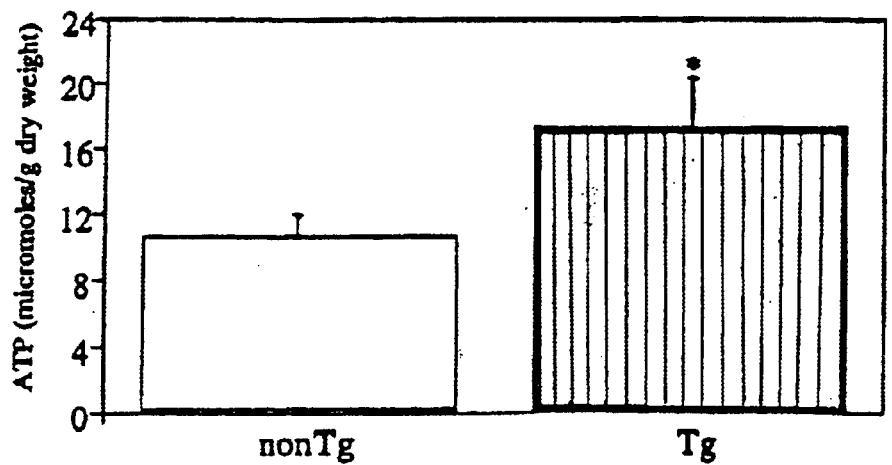

NMR analysis of $^{13}$C-β-hydroxybutyrate metabolism in Tg PD-ABAD mice. Tg PD-ABAD and control mice were infused with D-[2,4-$^{13}$C]-3-hydroxybutyrate. $^{13}$C NMR spectra of cerebral cortical extracts from Tg PD-ABAD and nonTg littermate control (the latter spectra are not shown) mice illustrate labelling of glutamate and glutamine in the C-4, C-3 and C-2 positions, as well as GABA (γ-aminobutyric acid) in the C-2 position (FIG. 6A), consistent with entry of [$^{13}$c]-β-hydroxybutyrate via 2-[$^{13}$C]-acetyl-CoA into the TCA cycle. The intensity of glutamate and glutamine C-4 resonance was 50% and 20% greater, respectively, in Tg PD-ABAD mice compared with nonTg littermates (FIG. 6B). The glutamate to glutamine ratio, based on C-4 resonance area, was 3.6±0.3 in nonTg versus 2.1±0.4 in Tg PD-ABAD mouse brains (P<0.03). These data suggest that glutamine synthesis is more efficient in Tg PD-ABAD mouse brain compared with controls. The area of the $^{13}$C-labelled C-2 resonance of GABA was also greater in Tg PD-ABAD mice (4.8±0.3) than in nonTg controls (2.2±0.5; p<0.04). Such increased labelling of GABA is consistent with enhanced conversion of labelled glutamate to GABA in brains of Tg mice. $^1$H NMR analysis of these extracts revealed that the fractional enrichment in glutamate C-4 was significantly greater in Tg PD-ABAD (58±5%) than in nonTg littermates (38±7%; P<0.03). As might be expected from the increased utilization of exogenous β-hydroxybutyrate, measurement of basal ATP levels in cerebral cortex of Tg PD-ABAD mice fasted overnight showed a statistically significant increase compared with nonTg littermates (FIG. 6C). Similarly, levels of β-hydroxybutryate in the brains of Tg PD-ABAD mice were lower, compared with nonTg controls in view of its increased utilization in the presence of higher levels of neuronal ABAD (see FIG. 7D, animals not subjected to stroke). Thus, Tg PD-ABAD mice provide a means of detecting ABAD function because of their enhanced metabolism of exogenous β-hydroxybutyrate and their increased levels of ATP. These mice could provide a useful system for testing the effect of ABAD inhibitors on neurons in the context of an intact blood-brain barrier.

Induction of stroke in Tg PD-ABAD mice. In order to assess the possible contribution of ABAD to ischemic stress, Tg PD-ABAD and age-matched nonTg littermate control mice were subjected to a 45 min period of transient middle cerebral artery occlusion followed by a 24 hr period for evolution of the cerebral infarct. These studies utilized a protocol which we have found to provide reproducible stroke volumes and functional data (neurologic deficit scores, cerebral blood flow)[32-35]. Levels of ABAD increased an additional ≈2-fold in Tg PD-ABAD mice after stroke, versus with uninstrumented Tg PD-ABAD mice. Compared with nonTg littermate controls, Tg PD-ABAD mice displayed strokes of smaller volume and lower neurologic deficit scores (consistent with better maintenance of neurologic function)(FIGS. 7A–B). In contrast, there was no change in cerebral blood flow comparing the Tg and nonTg animals (not shown), consistent with a direct effect of ABAD on neurons, as ABAD was overexpressed in neurons by the PDGF B chain promoter. Analysis of cerebral cortex from Tg animals showed increased ATP and decreased lactate levels compared with nonTg controls (FIG. 7C). In addition, β-hydroxybutyrate levels were lower in animals subjected to cerebral ischemia, and this finding was much more pronounced in Tg PD-ABAD mice compared with nonTg littermate controls (FIG. 7D). These data are suggested better maintenance of energy reserve and substrate metabolism in Tg PD-ABAD mice subject to ischemia.

Characterization of Tg PD-ABAD/hAPP mice. The increased expression of ABAD in AD brain, compared with age-matched non-demented control brain, suggested that the receptor might be associated with AD pathology. Consistent with this hypothesis, our pilot studies with Tg hAPP mice displayed increased levels of ABAD in cerebral cortex by 4 months of age, which is prior to plaque formation (not shown). Tg hAPP mice are especially useful for studies to assess the effect of introduction of the PD-ABAD transgene since they have been characterized in previous studies with respect to neuropathologic and electrophysiologic properties.

Figure 8:
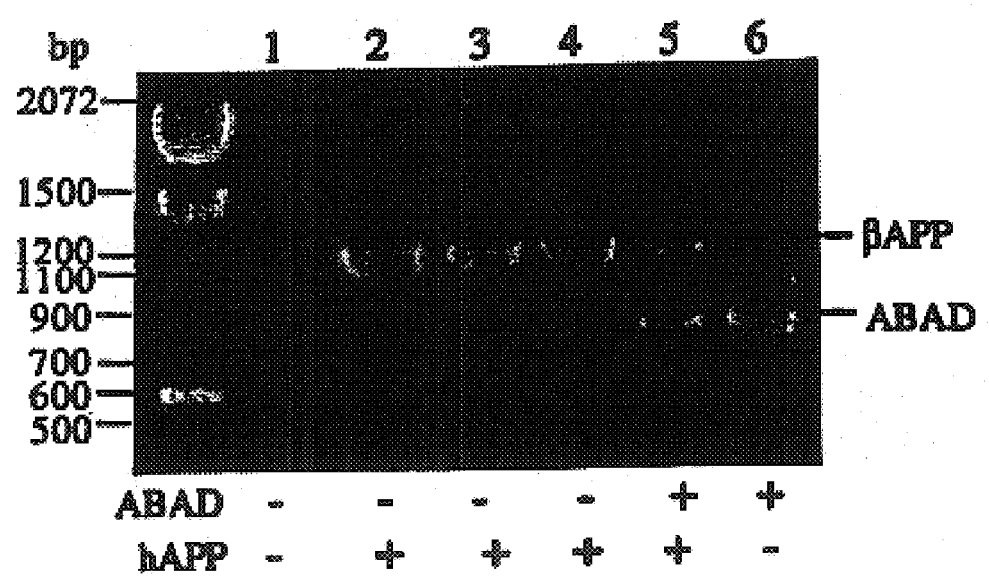
FIG. 8. Identification of a double transgenic mouse over-expressing ABAD and mutant human APP by PCR.
Figures 9A, 9B, 9C:
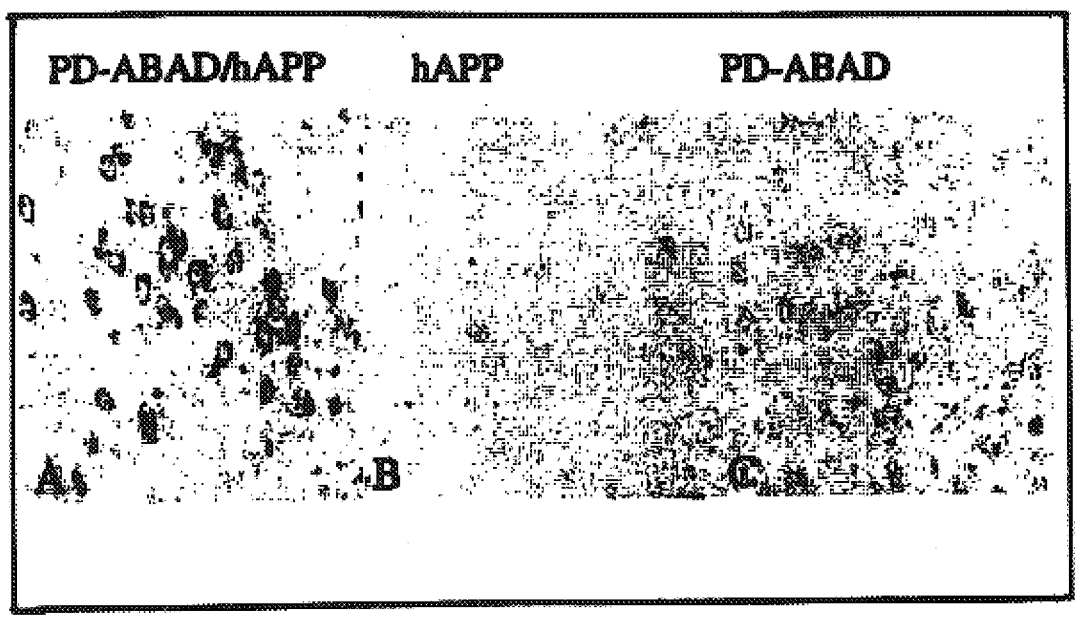
FIGS. 9A–E. Expression of 4-hydroxynonenal-lysine epitopes in cerebral cortex from double Tg mice overexpressing ABAD and mutant human APP (hAPP) termed Tg PD-ABAD/hAPP.
Figures 9D, 9E:
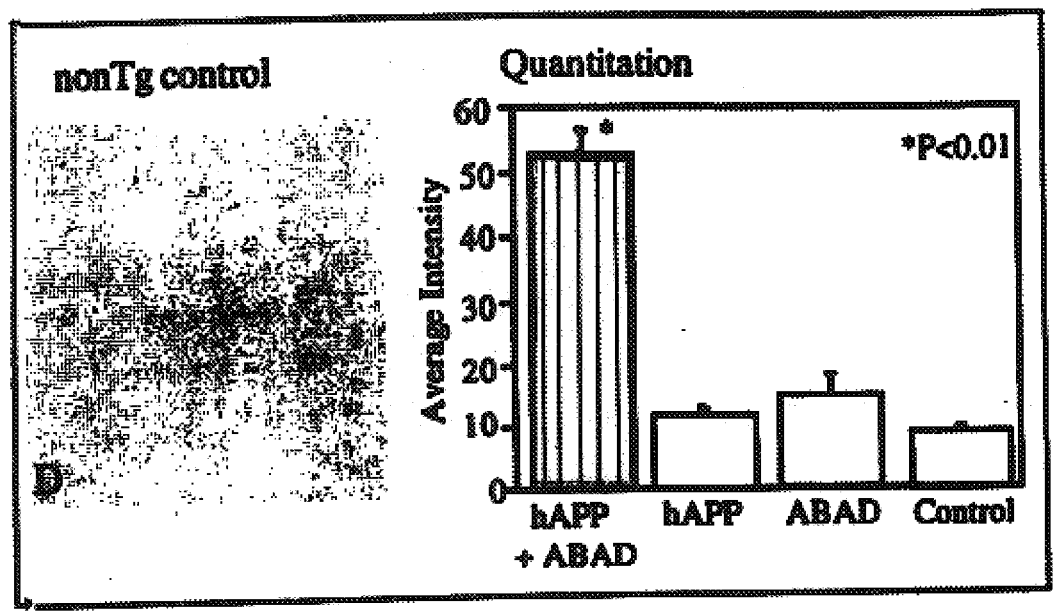

If ABAD exacerbated Aβ-induced neuronal stress, we reasoned that expression of high levels of ABAD at early times in the brains of animals expressing the hAPP transgene might result in magnified evidence of cytotoxicity (the transgenic model introduces higher levels of ABAD than were present in Tg hAPP mice alone, and thus, potentially represents a model of exaggerated effects of ABAD). Crossbreeding studies were performed and double transgenic mice were identified by PCR using primers specific for the PD-ABAD transgene and the hAPP transgene. Results of a representative PCR analysis are shown in FIG. 8 demonstrating amplicons for both the PD-ABAD and hAPP genes in the double-transgenic animals versus single transgenics and nontransgenic littermate controls. The double transgenic mice have been termed Tg PD-ABAD/hAPP mice. Double transgenic mice were observed for three-four months and evidence of neuronal stress was then analyzed by studying expression of 4-hydroxynonenal (HNE; FIG. 9) and heme oxygenase type I (HO-1; FIG. 10). HNE-lysine epitopes were determined by immunostaining with a monoclonal antibody followed by image analysis. Increased levels of HNE antigen were evident in the cerebral cortex of Tg PD-ABAD/hAPP by 4 months of age, compared with single transgenics and nontransgenic littermate controls (FIG. 9). Level of HO-1 were also increased in brains of double transgenic animals based on Northern analysis (FIG. 10A) and semiquantitative immunohistochemistry (FIG. 10B) in each case on samples of cerebral cortex.

Figure 11B:
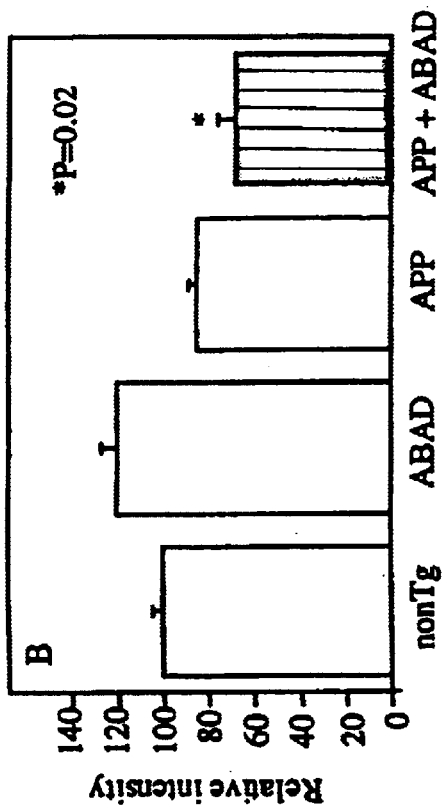
FIGS. 11A–11B. Semiquantitative analysis of synaptophysin immunoreactivity in hippocampus of Tg PD-ABAD/hAPP, Tg PD-ABAD, Tg hAPP, and nontransgenic littermate control mice at 4 months of age.
Figure 11A:
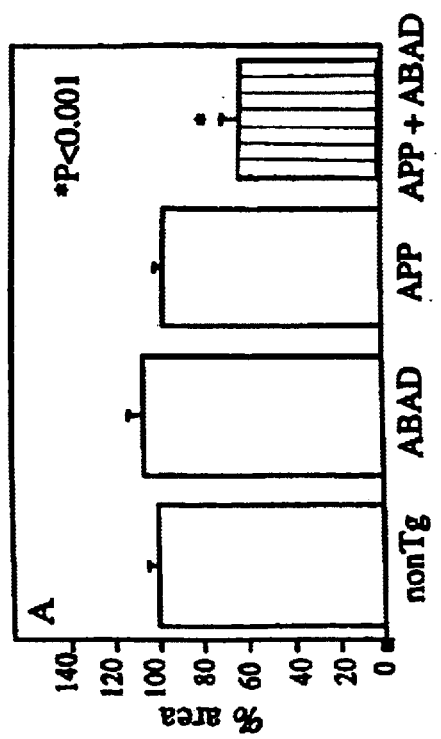
Figure 12B:
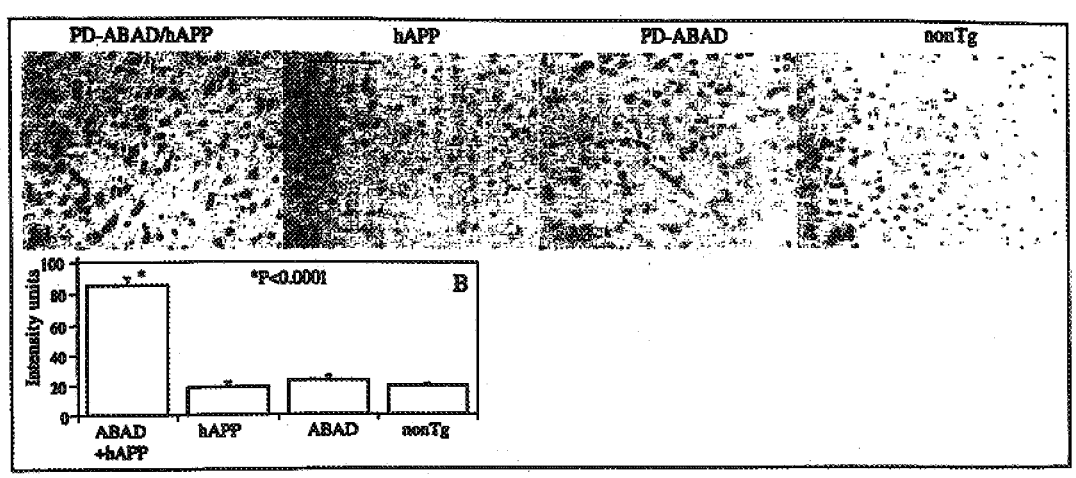

These data were consistent with increased neuronal stress in Tg PD-ABAD/hAPP mice, but did not indicate whether the outcome of this stress would be neuroprotection or neurotoxicity. To analyze this situation neuropathologic studies were performed, and study of markers more clearly associated with toxicity, such as synaptophysin and activated caspase 3, was undertaken. Immunostaining of hippocampus (lacunosum moleculare layer) from double transgenic mice (age 3–4 months) with antibody to synaptophysin demonstrated a reduction in the area of neuropil occupied by synaptophysin-labeled presynaptic terminals, as well as the intensity of staining (FIG. 11). Similar studies with antibody to MAP-2 showed a reduction in the area of neuropil occupied by MAP-2-labeled dendrites (not shown). Although stereologic studies will be required to determine actual neuronal loss, these results are consistent with evidence of neurotoxicity. Consistent with this impression, analysis of older double transgenic mice (8–9 months of age) showed increased staining with an antibody selective for the activated form of caspase 3 (FIG. 12) in brains of double transgenic mice compared with the other groups.

Figures 13A, 13B:
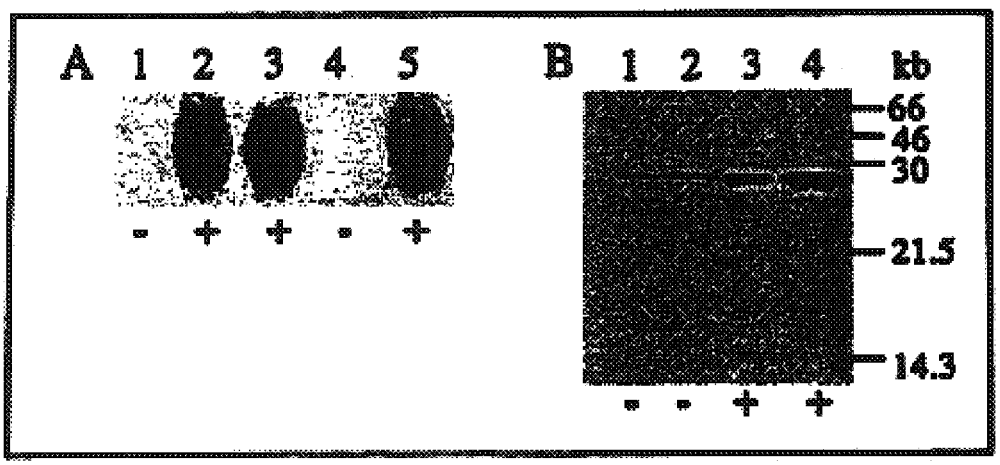
FIGS. 13A–13B. Northern analysis (FIG. 13A) and immunoblotting (FIG. 13B) of E16 cortical neuron cultures with $^{32}$P-labelled human ABAD cDNA (FIG. 13A) or anti-human ABAD IgG (FIG. 13B). (+) indicates neurons obtained from Tg PD-ABAD mice and (–) indicates neurons are from nontransgenic littermate controls.

Characterization of neurons isolated from Ta PD-ABAD mice. Neuronal cultures were made from the cerebral cortex from E16 mouse embryos. These cultures were >90% neurons based on staining with anti-neircilament antibody (not shown). Cultured neurons displayed high levels of ABAD expression based on Northern analysis and immunoblotting [(FIG. 13)].

Discussion

We have described the generation of Tg PD-ABAD mice which display increased expression of full-length ABAD in neurons. The use of these mice to analyze the contribution of ABAD to cellular responses in vitro and in vivo can be summarized according to three general categories:

1) analysis of neurons cultured from embryos of Tg PD-ABAD mice. Since neurons are nondividing cells and can only be transfected successfully with viral-based systems (which can alter cellular properties themselves), the cultured neurons from Tg PD-ABAD mice provide an unique system in which neurons overexpress human ABAD. These cells can be used to analyze the consequences of ABAD expression in an Aβ-rich environment for neuronal function.

2) Tg PD-ABAD mice can be used to directly assess the effect of ABAD overexpression in settings such as, but not limited to, stroke (described above), viral/bacterial infections, other models of brain inflammation (such as experimental autoimmune encephalitis) etc.

3) Tg PD-ABAD mice can be crossbred with other transgenic animals, such as Tg hAPP to determine the consequences of ABAD overexpression in an environment in which the other transgene creates an unique environment in the brain. For example, the Tg hAPP mouse results in increased levels of Aβ. In this setting, the consequences of increased levels of Aβ in the context of neurons bearing elevated levels of ABAD can be studied.

In each case, the in vitro and in vivo systems based on Tg PD-ABAD mice or cells derived from them are ideal for studying ABAD inhibitors, as well as for dissecting contributions of ABAD to physiologic/pathophysiologic outcomes.

EXAMPLE 2

Double Transaenic Mice Overexpressing ABAD and mutAPP (V717F, K670M, N671L) Show an Impairment of Hippocampal Long-Term Potentiation Amyloid-beta peptide (Aβ) is the principal component of the extracellular deposits in Alzheimer's disease. However, means by which Aβ perturbs cellular functions are still unknown. It has been shown recently that Aβ binding alcohol dehydrogenase (ABAD), in an Aβ-rich environment is permuted from a protective enzyme to a cofactor enhancing Aβ toxicity. In order to study the interaction of ABAD with mutAPP, double transgenic mice overexpressing both proteins in neurons under control of the PDGF-B chain promoter have been generated. Here, an investigation of basal synaptic transmission and synaptic plasticity is shown in hippocampal slices from these animals. To measure basal synaptic transmission, we generated input-output curves by plotting the stimulus voltage against the slope of the field EPSP. It was found that a 47% reduction in basal synaptic transmission in 10-month old mutAPP/ABAD mice (n=12) compared with wild type animals (n=11 slices, P<0.001). Transgenics overexpressing either mutAPP or ABAD alone did not show any change. Next, LTP was examined after a theta-burst stimulation in CA1 and observed that wild-type mice showed a 159% (n=10 slices) increase compared to baseline values 60 min after the stimulation, whereas mutAPP/ABAD littermates showed a 130% increase (n=9 slices, P<0.05). Single ABAD and mutAPP showed values comparable to wild-type animals. Thus, simultaneous overexpression of ABAD and mutAPP dramatically alters both basal synaptic transmission and synaptic plasticity.

EXAMPLE 3

Enhanced Neuronal Stress and Cytotoxicity in Double Transgenic Mice With Targeted Overexpression of ABAD and Mutant Amyloid Precursor Protein (mutAPP)

Amyloid-beta peptide binding alcohol dehydrogenase (ABAD) is an intracellular enzyme capable of binding amyloid-beta peptide and promoting cell stress in vitro. To examine properties of ABAD in vivo, transgenic (Tg) mice overexpressing ABAD under control of the PDGF B chain promoter (Tg PD-ABAD) were made. These animals demonstrated increased ABAD antigen in neurons of cerebral cortex and hippocampus. Tg PD-ABAD mice were crossed with animals overexpressing a minigene encoding hAPP 695, 751 & 770 bearing mutations linked to familial Alzheimer's disease (Tg hAPP) to generate progeny which are double transgenics (Tg PC-ABAD/hAPP). By 4 months of age, Tg PD-ABAD/hAPP mice displayed increased neuronal stress, elevated 4-hydroxynonenal immunoreactivity (3-fold increased; p<0.01) and heme oxygenase type 1 (3-fold) were observed in cerebral cortex of double transgenics compared with other groups. Semiquantitative immunohistochemistry for synaptophysin and microtubule-associated protein 2 showed decreases in both cases (25% and 25–30% respectively, compared with other groups; p<0.001). Evidence of neurotoxicity was also suggested by increased levels of activated caspase 3 antigen in cortical neurons (3–4-fold increase compared with the other groups; p<0.001). These data indicate that targeted neuronal overexpression of ABAD and hAPP exaggerates cell stress and promotes cytotoxicity.

EXAMPLE 4

Amyloid Beta-peptide Binding Alcohol Dehydrogenase is a Component of the Cellular Response to Nutritional Stress Amyloid β-peptide Binding Alcohol Dehydrogenase (ABAD) is a member of the family of short-chain dehydrogenase/reductases whose distinctive properties include the capacity to bind amyloid beta-peptide (Aβ) and enzymatic activity towards a broad array of substrates including n-isopropanol and β-estradiol. In view of ABAD's wide substrate specificity and high activity on L-β-hydroxyacyl CoA derivatives, we asked whether it might also catalyze the oxidation of the ketone body D-3-hydroxybutyrate. This was indeed the case, and oxidation proceeded with $K_m$ _3.7 mM and $V_{max}$ _4 nmol/min/mg protein. When placed in medium with D-β-hydroxybutyrate as the principal energy substrate, COS cells stably transfected to overexpress wild-type ABAD (COS/wtABAD) better maintained 3-(4,5-dimethylthiazol-2-yl)-2,5-diphenyl tetrazolium bromide reduction, cellular energy charge and morphologic phenotype, compared with COS/vector cells. Using a severe model of metabolic perturbation, transgenic mice with targeted neuronal expression of ABAD subjected to transient middle cerebral artery occlusion showed strokes of smaller volume and lower neurologic deficit scores in parallel with increased brain ATP and decreased lactate, compared with nontransgenic controls. These data suggest that ABAD contributes to the protective response to metabolic stress, especially in the setting of ischemia.

Introduction

Recent studies of familial Alzheimer's disease have provided support for a close relationship between accumulation of amyloid beta-peptide (Aβ)[1], especially the longer form, Aβ(1–42), and development of cerebral dysfunction leading to dementia (1–4). In sporadic Alzheimer's disease (AD), there is an emerging view that decreased clearance of Aβ, possibly mediated by a pathway involving low density lipoprotein receptor-related protein, apoE and/or α₂-macroglobulin, may contribute to the Aβ-rich environment that disturbs cellular properties (5–8). However, much remains to be learned about the pathways through which Aβ actually induces cellular stress. In the presence of high concentrations of Aβ (micromolar range), generation of oxidants and changes in calcium homeostasis feed into cell death pathways (9–12).

[1] Abbreviations: Aβ, amyloid-β peptide; AD, Alzheimer's disease; ABAD, Aβ binding alcohol dehydrogenase; CoA, Coenzyme A; GABA, γ-amino butyric acid; MCA, middle cerebral artery; MTT, 3-(4,5-dimethylthiazol-2-yl)-2,5-diphenyl tetrazoliun bromide; PD, platelet-derived growth factor B chain; SDR, short-chain dehydrogenase/reductase; TCA, tricarboxylic acid cycle; and, Tg, transgenic.

In order to understand mechanisms which might underlie Aβ-induced cell stress, rather than rapid induction of cell death, we have sought cell-associated cofactors capable of magnifying the effects of the amyloid peptide on target cells.

We reasoned that such cofactors might be relevant to early phases of AD when neuronal dysfunction is evolving, but changes are still reversible.

Amyloid β-peptide Binding Alcohol Dehydrogenase (ABAD) is a member of the family of short-chain dehydrogenase/reductases (SDR)(13,14). It shares features with other members of this family, such as the requirement for a dinucleotide cofactor, nicotinamide adenine dinucleotide (NAD[H]), and a Rossman-fold structural topology with an invariant sequence, Tyr-X-X-X-Lys, corresponding to residues 168–172 in ABAD, all of which are required for enzymatic activity (15). However, it is distinct from other members of the family in terms of its ability to bind Aβ (13,14), and its ability to use a broad array of substrates, including linear alcohols, 3-hydroxyacyl-Coenzyme A (CoA) derivatives, and steroids (such as 17β-estradiol)(13, 14,16–19). In an Aβ-rich environment, ABAD appears to potentiate cell stress induced by the amyloid peptide, as evidenced by increased generation of 4-hydroxynonenal-lysine and malondialdehyde-lysine epitopes and induction of DNA fragmentation (14). Although these observations suggest a "dark side" of ABAD potentially contributing to the pathogenicity of Aβ-induced cellular dysfunction, we reasoned that ABAD is likely to have other properties relevant to normal physiology. Consistent with this concept, inactivation of the Drosophila counterpart of ABAD, termed scully, resulted in a lethal phenotype with multiple developmental abnormalities (20).

These broad enzymatic properties of ABAD suggested that it might facilitate utilization of ketone bodies, by promoting the generation of acetyl-CoA to feed into the tricarboxylic acid (TCA) cycle. This led us to consider a role for ABAD in the cellular response to nutritional/metabolic stress. For example, ketone bodies can reach appreciable concentrations (3–6 mM) in fasted nonhuman primates, both neonatal and infant animals (21), as well as during starvation in normal humans/adult animals (22–23). Under these conditions, the oxidation of β-hydroxybutyrate becomes the dominant source for energy production in brain (21–23). In the current study, we demonstrate that ABAD does promote utilization of ketone bodies in a cellular environment, probably at the level of both β-hydroxybutyrate. Furthermore, overexpression of ABAD in COS cells, which have low endogenous levels of this enzyme, maintains cellular functions under conditions where β-hydroxybutyrate is the principal energetic substrate. Using NMR to analyze [$^{13}$C]-β-hydroxybutyrate metabolism, ABAD-transfected COS cells displayed increased flux of acetyl-CoA through the TCA cycle. Since ischemia is a severe metabolic stress, a murine stroke model in transgenic mice was employed to determine consequences of overexpressing ABAD in cortical neurons. ABAD transgenic mice demonstrated a protective phenotype with _40% reduction in stroke volume and improvement in neurologic deficit scores. Overexpression of ABAD in Tg mice was associated with increased flux of acetyl-CoA through the TCA cycle and increased ATP in cerebral cortex following infusion of β-hydroxybutyrate. These data indicate that expression of ABAD confers a protective phenotype in response to acute metabolic stress, such as that imposed by ischemia, and provide a starting point for further analysis of ABAD's properties in complex biologic systems.

Materials and Methods

Recombinant ABAD and metabolism of β-hydroxybutyrate and β-hydroxybutyryl-CoA. ABAD was produced recombinantly in *E. coli* (BL21) and purified to homogeneity as described (14). D- and L-β-hydroxybutyrate and D/L-β-hydroxybutyryl-CoA were obtained from Sigma., ABAD reduction of DL-β-hydroxybutyryl-CoA employed ABAD (330 ng/ml), a range of β-hydroxybutyryl-CoA concentrations (20–1000 _M), and NAD$^+$ (1.2 mM; Sigma) in Tris (75 mM; pH 10)/KCl (75 mM)(17). The reaction was run for a total of 10 min at 30° C. under steady-state conditions (24), and the change in NADH absorbance at 340 nm was determined. ABAD reduction of either D- or L-β-hydroxybutyrate employed ABAD (150 _g/ml), a range of β-hydroxybutyrate concentrations (0.4–25 mM), and NADH (5 mM) in Tris (10 mM; pH 7.4)/NaCl (25 mM). β-hydroxybutyrate, NADH and Tris/NaCl were preincubated for 10 min at 37° C. Then, the enzyme was added, and the reaction was run for a total of 30 min at 30° C. under steady-state conditions as above, except that absorbance at 340 nm was determined every 5 min. Kinetic data were analyzed for Michaelis-Menton by PRISM (Scitech, San Diego, Calif.) to determine $K_m$ and $V_{max}$, and lines shown in the figures represent theoretical curves according to kinetic parameters calculated by the program. One unit of enzyme activity was defined as that which converts 1.0 _mol of substrate to product per min. All studies to determine kinetic parameters of ABAD were performed 3–5 times.

Generation and characterization of stably-transfected COS cells expressing ABAD. COS cells (ATCC; $10^5$ cells) were transfected with pcDNA3/(human) wild-type ABAD or mutABAD, or pcDNA3 alone (vector) previously linearized with SmaI, using lipofectamine (14). MutABAD, in which residues 168 (Y) and 172 (K) in the active site have been replaced by glycine, generating an enzymatically crippled enzyme, has been previously characterized (14). Forty-eight hours after transfection, cells were plated at 1:10–1:20 dilution in 100 mm dishes containing G418 (1 mg/ml), and, after 1–2 wks, single clones were isolated, cells were separated with trypsin, subject to limiting dilution and replated in medium containing G418 (1 mg/ml) for 2–4 wks. Cultures were then maintained in DMEM with fetal bovine serum (Gibco, Grand Island, N.Y.; 10%) and G418 (1 mg/ml), and ABAD expression was characterized as described below. For Northern blotting, total RNA was isolated using Trizol (Gibco) and run on 1% agarose gels, transferred to nitrocellulose, and hybridized with a full length $^{32}$P-labelled cDNA probe for ABAD (13,14). For immunoblotting, cell lysates, prepared by directly lysing cell pellets in SDS sample buffer, were subjected to SDS-PAGE (reduced; 12%) followed by transfer to nitrocellulose. The Blotto procedure was used (25); the first antibody was anti-ABAD peptide IgG (10 _g/ml), and the second antibody was peroxidase-conjugated goat anti-rabbit IgG (1:2000 dilution; Sigma, St. Louis Mo.) in the ECL secondary antibody/detection system (Amersham, Arlington Hts, Ill.). Anti-ABAD peptide IgG was prepared and characterized as described previously (13,14).

Subcellular fractionation of ABAD employed ultracentrifugation of cells disrupted by nitrogen cavitation bomb, as described (14). Following disruption, the lysate was clarified by centrifugation at 10,000×g for 15 min at 4° C., and the pellet was resuspended in buffer containing tris/HCl (10 mM; pH 8.0)/Nonidet P-40 (1%), NaCl (150 mM), EDTA (1 mM), aprotonin (1 _g/ml), and phenylmethylsulfonyl fluoride (1 mM). This material was centrifuged and fractionated through a series of sucrose steps (38, 30, and 20% sucrose prepared in HEPES (10 mM; pH 7.5/dithiothreitol [1 mM]). Layered fractions were collected as described (28), and each fraction (5 μg protein/lane) was analyzed by immunoblotting with anti-ABAD peptide IgG. The following markers of subcellular compartments were employed: RAGE for cell membranes (anti-RAGE IgG was prepared as described)(26, 27), GRP78/Bip for endoplasmic reticulum (antibody to GRP78/Bip was obtained from StressGen®, Victoria, Canada) (28), and cytochrome c for mitochondria (antibody to cytochrome c was obtained from StressGen®). The mitochondria-rich fraction was also prepared as described by Du et al.(29).

$^{13}$C-NMR spectroscopy. $^{13}$C NMR spectroscopy is a powerful technique for measuring substrate metabolism in tissue and cell culture (30–38). Addition to culture supernatant or perfusing organs with D-[2,4-$^{13}$C]-3-hydroxybutyrate results in the [$^{13}$C]-labelling of TCA cycle intermediates from labeled acetyl CoA (36,37). Although TCA cycle intermediates are usually present at concentrations too low to be observed by NMR spectroscopy, glutamate, which is present at millimolar concentrations, is in rapid exchange with α-ketoglutarate via aminotransferase reactions. Thus, if [$^{13}$C]-labeled acetyl CoA enters the TCA cycle, the $^{13}$C-label will be detectable as [$^{13}$C]-glutamate. For experiments with cultured cells ($10^7$ cells/NMR determination), D-[$^{13}$C]-β-hydroxybutyrate (10 mM) was added to DMEM (without glucose or pyruvate) and dialyzed fetal calf serum (10%). For in vivo studies, D-[$^{13}$C]-β-hydroxybutyrate was infused intravenously as follows over 60 min: 0.75 M [$^{13}$C]-β-hydroxybutyrate administered as a bolus (0.05 ml) followed by a constant infusion with a total volume of 1.5 ml (38). At the end of the infusion, brain samples were freeze-clamped under liquid nitrogen and stored at −80° C. Frozen tissue (sample size, 92±6 and 88±11 mg, for Tg and nonTg mice, respectively) was extracted with perchloric acid, neutralized with sodium hydroxide as described (35–37), and homogenates were lyophilized and resuspended in $D_2O$ for NMR analysis. For cell culture studies, culture supernatants and lysates were extracted with perchloric acid followed by neutralization and lyophilization as above.

High resolution carbon spectra were acquired on a Bruker 500 MHz spectrometer, using a 10 mm broad-band probe tuned to 125.77 MHz. Field homogeneity was optimized by shimming on the $D_2O$ lock signal. Spectra were obtained using a 25 KHz sweep width, with 45° pulse and 25 interpulse delay. Heteronuclear decoupling was performed using a Waltz sequence. Each spectrum represents a total of 17,920 scans. The assignment of $^{13}$C resonances was based on previously published studies (33,34,36–38). Glutamate peak areas were determined using Bruker NMR software, and are expressed as ratios with the summed area of the [2,4-$^{13}$C]β-hydroxybutyrate peaks. In brain extracts, the area measurements for glutamate, glutamine and γ-amino butyric acid (GABA) are compared with spectra obtained from an external standard solution ([$^{13}$C]-acetate, 0.1 M) using the same acquisition parameters as above. The $^{13}$C NMR spectra of standard solutions of glutamine and GABA were obtained to confirm chemical shifts of these compounds in the brain extracts.

$^1$H NMR Spectroscopy. Water pre-saturation experiments were acquired on the GE500 MHz spectrometer using a 5 mm inverse detection probe ($^1$H observe, with broad band decoupling capabilities). With a sweep width of 5 KHz, a 45° pulse width, and the carrier frequency set on the $H_2O$ peak for a 1 s pre-saturation pulse, $^1$H spectra were obtained for 256 total scans. Presaturation experiments were performed both with and without heteronuclear $^{13}$C decoupling (for assessing the fractional enrichment in glutamate), centered at 40 ppm, using a Waltz sequence.

The region between 2.6–2.0 ppm reveals proton resonances from the C-4 of glutamate. Although the proton resonances corresponding to [$^{12}$C-4]glutamate are resolvable, the $^1$H satellites corresponding to [$^{13}$C-4] glutamate are obscured by other nearby peaks. Accordingly, the fractional enrichment of glutamate cannot be determined by measuring the areas of the proton peaks bound to labeled and nonlabeled carbons, as is the case with lactate (32). However, the enrichment of glutamate C-4 may be determined from the increase in intensity of the C-4 glutamate proton resonances following heteronuclear $^{13}$C-decoupling, as these resolvable resonances then correspond to the sum of protons from labeled and nonlabeled glutamate (32).

Assays of Cellular Function: MTT reduction and measurement of cellular energy charge. Reduction of 3-(4,5-dimethylthiazol-2-yl)-2,5-diphenyl tetrazolium bromide (MTT) was studied and phase contrast micrographs of COS cells were made as previously described (13,39). Measurement of cellular energy charge was also performed by previous methods (40). In brief, cultured cells previously incubated in D-β-hydroxybutyrate, DMEM without glucose or sodium pyruvate (Gibco/BRL), and dialyzed fetal calf serum (10%; Gibco/BRL) were washed three times in phosphate-buffered saline. Adenine nucleotides were extracted with perchloric acid (1 M), and subjected to centrifugation through a layer of bromododecane. The supernatant was neutralized with potassium hydroxide and subjected to reversed-phase HPLC (Microsorb C18; Rainin Instruments Co., Woburn, Mass.). The column eluate was monitored at an absorbance of 254 nm, and nucleotide concentration was calculated from the peak area using ChromatoPack CR-4A (Shimadzu Seiki, Kyoto, Japan). At each point the energy charge was calculated as described (41).

Generation and characterization of ABAD transgenic mice. The platelet-derived growth factor (PDGF) B-chain promoter was used to drive overexpression of ABAD in neurons of the central nervous sytem of transgenic (Tg) mice (42). Transgene constructs were prepared using a previously described vector (43,44). Briefly, the CMV immediate/early promoter was excised from the commercial expression vector pCI (Promega, Madison Wis.), and replaced with an oliognucleotide polylinker. The PDGF B-chain promoter fragment was mobilized as an Xba1 fragment (42) and cloned into a unique Spe1 site designed within the synthetic linker. The full-length human ABAD cDNA was inserted into the NotI site of the original polylinker. A 3 kb fragment containing the promoter, cDNA and required other sequences was then excised from the plasmid backbone as BamHl fragment and microinjected mouse B6CBAF$_1$/J oocytes. The latter were implanted into pseudopregnant females and mated with B6CBAF$_1$/J males resulting in the generation of four founders. These were used to produce lines, which were backcrossed eight times into the C57BL6 background. Tg PD-ABAD mice were identified by Southern blotting, and expression of the transgene was monitored by Northern and Western blotting, and immunostaining. Southern blotting was performed on DNA extracted from mouse tails, and hybridization was performed with $^{32}$P-labelled cDNA probe for ABAD. Northern and immunoblotting utilized the same procedures as above, except that tissue was homogenized in the presence of Trizol (RNA) or in lysis buffer (Tris/HCl, 20 mM, pH 7.4; Triton X-100, 1%; phenylmethylsulfonylfluoride, 2 mM; EDTA, 1 mM; aprotonin, 10 _g/ml; leupeptin, 10 _g/ml; 1 ml of buffer per 0.5 gm of tissue). Note that immunoblotting and immunostaining of brain tissue from Tg PD-ABAD mice used anti-human ABAD peptide IgG which appears to be preferentially immunoreactive with human ABAD, the latter encoded by the transgene (13). Immunostaining was performed on paraformaldehyde (4%)-embedded sections (6 _m) which were deparaffinized and dehydrated, and then stained with rabbit anti-human ABAD peptide IgG (8.5 _g/ml) followed by goat anti-rabbit biotin-conjugated IgG and ExtrAvidin-conjugated with alkaline phosphatase (Biotin ExtrAvidin kit; Sigma, St. Louis Mo.).

Murine stroke model. Mice (C57BL6/J, male) were subjected to stroke according to previously published procedures (45) and in accordance with guidelines of the American Academy of Accreditation of Laboratory Animal Care (AAALAC). Following anesthesia, the carotid artery was accessed using the operative approach previously described in detail (46), including division/coagulation of the occipital and pterygopalatine arteries to obtain improved visualization and vascular access. A nylon suture was then introduced into the common carotid artery, and threaded up the internal carotid artery to occlude the origin of the right middle cerebral artery (MCA). Nylon (polyamide) suture material was obtained from United States Surgical Corporation (Norwalk, Conn.), and consisted of 5.0 nylon/13 mm length for 27–36 g mice, and 6.0 nylon/12 mm length for 22–26 g mice. After 45 minutes of occlusion, the suture was withdrawn to achieve a reperfused model of stroke. Although no vessels were tied off after the suture was removed, the external carotid arterial stump was cauterized to prevent frank hemorrhage. Measurements of relative cerebral blood flow were obtained as previously reported (45–48) using a straight laser doppler flow probe placed 2 mm posterior to the bregma, and 6 mm to each side of midline using a stereotactic micromanipulator, keeping the angle of the probe perpendicular to the cortical surface. These cerebral blood flow measurements, expressed as the ratio of ipsilateral to contralateral blood flow, were obtained at baseline, and immediately prior to MCA occlusion, 45 minutes after MCA occlusion, and at several time points after withdrawal of the occluding suture. Measurement of Cerebral Infarction Volumes: After 24 hours, animals were euthanized and their brains rapidly harvested. Infarct volumes were determined by staining serial cerebral sections with triphenyl tetrazolium chloride and performing computer-based planimetry of the negatively (infarcted) staining areas to calculate infarct volume (using NIH image software). Neurological Exam: Prior to giving anesthesia, mice were examined for neurological deficit 23 h after reperfusion using a four-tiered grading system: a score of 1 was given if the animal demonstrated normal spontaneous movements; a score of 2 was given if the animal was noted to be turning towards the ipsilateral side; a score of 3 was given if the animal was observed to spin longitudinally (clockwise when viewed from the tail); and, a score of 4 was given if the animal was unresponsive to noxious stimuli. This scoring system has been previously described in mice (45–47), and is based upon similar scoring systems used in rats (49). Immunostaining of cerebral cortex following induction of stroke in wild-type mice was performed as described above using a rabbit polyclonal antibody made using purified recombinant murine ABAD as the immunogen. Quantitation of microscopic images was accomplished with the Universal Imaging System.

ATP and lactate/pyruvate ratio were determined in cerebral cortex from control mice, and from ischemic versus nonischemic hemispheres of mice subjected to ischemia (measurements were made 24 hrs after induction of ischemia). Perchloric acid-extracted cerebral cortex was neutralized with sodium hydroxide and the ATP in the extract was measured using HPLC techniques (50). Lactate, β-hydroxybutyrate and pyruvate levels in the neutralized extracts were measured using established assays (51).

Results

ABAD metabolism of β-hydroxybutyrate. The broad enzymatic properties of ABAD as an oxidoreductase suggested that it might facilitate cellular utilization of ketone bodies, such as D-β-hydroxybutyrate, a major energetic substrate during nutritional deprivation in vivo. First, we tested DL-β-hydroxybutyryl-CoA, a known substrate of bovine liver-derived hydroxyacyl-CoA type II (HADH II)/ABAD (17), with our purified E. Coli-derived human recombinant ABAD. The latter result, obtained with a racemic DL mixture of β-hydroxybutyryl CoA, was similar to that observed previously with the bovine liver HADH II (17). Using the same preparation of recombinant ABAD, we then studied D-β-hydroxybutyrate. In a purified system, ABAD is clearly more effective with β-hydroxybutyryl-CoA as a substrate (presumably this is the L-form, which is an intermediate in the fatty acid β-oxidation pathway in mitochondria). However, depending on physiological conditions, certain substrates may turn out to be more abundant, such as D-β-hydroxybutyrate during periods of starvation when levels of ketone bodies are elevated and, thus, could become relevant. In fact, plasma levels of β-hydroxybutyrate are reported to reach the millimolar range in animals and humans subject to nutritional deprivation (21–23). Furthermore, β-hydroxybutyryl CoA generated by acyl CoA dehydrogenase is another likely substrate of ABAD in a cellular milieu rich in β-hydroxybutyrate. Thus, ABAD would appear to have the potential to be pivotal for enhancing metabolism of β-hydroxybutyrate.

Characterization of COS cells stably-transfected to overexpress ABAD. COS cells provided a useful model to test our concept that ABAD modulated the cellular response to nutritional stress because of their low endogenous expression of ABAD; low levels of mRNA were present and no antigen was detectable in lysates of wild-type COS cells. Following stable transfection with either pcDNA3 alone (vector), pcDNA3/wtABAD (encoding wild-type ABAD) or pcDNA3/mutABAD (encoding a mutant form of ABAD devoid of enzymatic activity; 14), cells were plated at limiting dilution and clones were prepared. Three types of clones were established, those expressing vector alone (COS/vector), wild-type ABAD (COS/wtABAD) and mutant ABAD (COS/mutABAD). Studies were performed with three representative clones of each type of stably-transfected COS cell. Whereas COS/vector cells displayed low levels of ABAD transcripts and antigen, comparable to control COS cells, COS/wtABAD cells showed high levels of ABAD mRNA and antigen. Subcellular fractionation studies on COS/wtABAD cells demonstrated the presence of ABAD both in fractions 1–2 enriched for the endoplasmic reticulum marker GRP78 and in the mitochondrial pellet (fraction 6) containing cytochrome c. Similar experiments performed with COS/mutABAD stable transfectants displayed high levels of ABAD transcripts and antigen in a distribution analogous to that seen in COS/wtABAD cells. These data indicated that in COS/ABAD stable transfectants, the enzyme is present at the same sites previously observed in cells endogenously expressing ABAD or those transiently transfected to overexpress ABAD (13,14, 16,19).

ABAD and the response of COS cells to nutritional stress. In view of ABAD metabolism of D-β-hydroxybutyrate, we tested whether ABAD-transfected COS cells displayed enhanced ability to sustain nutritional stress in an environment where ketone bodies provided the principal energetic source. When COS/vector cells were placed in medium devoid of glucose and supplemented only with dialyzed serum and β-hydroxybutyrate, cellular functions became compromised. In the presence of D-β-hydroxybutyrate (10 mM), reduction of MTT was suppressed by days 4–5 and cellular energy charge decreased in parallel. Phase contrast microscopy showed COS/vector cells, initially with a spread morphology on the growth substrate, to become rounded up and toxic in appearance after four days under these conditions. Similar results were obtained when COS/vector cells were replaced with wild-type COS cells, and the same studies described above were performed (not shown). In contrast, COS/wtABAD cells better maintained MTT reduction and cellular energy charge in the presence of β-hydroxybutyrate. These changes in cellular properties were parallelled by maintenance of the morphologic phenotype of COS/wtABAD cells, compared with COS/vector transfectants in the presence of β-hydroxybutyrate. The effect of β-hydroxybutyrate to maintain cellular functions in COS/wtABAD cells was dose-dependent, as shown using the MTT reduction assay, and reached a plateau by 10 mM. Furthermore, experiments with lower concentrations of β-hydroxybuyrate (_2.5 mM) displayed less effective maintenance of cellular properties with COS/wtABAD cells (not shown). The requirement for enzymatically intact ABAD (wtABAD) for enhanced survival of COS/wtABAD cells in the presence of β-hydroxybutyrate was shown by experiments performed with COS/mutABAD cells. Though the crippled enzyme (mutABAD) was expressed at similar levels and with a similar subcellular distribution as the wild-type enzyme (the latter in COS/wtABAD cells), COS/mutABAD cells responded to glucose replacement with β-hydroxybutyrate as did CoS/vector cells; there was a steady decline in MTT reduction and cellular energy charge.

NMR studies were performed on cells incubated with [$^{13}$C]-D-β-hydroxybutyrate (labelled in the C-2 and C-4 positions) to determine the effect of ABAD on the metabolism of the COS/wtABAD transfectants in medium devoid of glucose. [$^{13}$C]-labelled β-hydroxybutyrate enters the TCA cycle as [$^{13}$C-2]-labelled acetyl-CoA and is metabolized to α-ketoglutarate. Thus, C-4 gets labelled in the first turn of the TCA cycle, and, subsequent, labelling occurs in the C-3 and C-2 positions. As α-ketoglutarate is in rapid equilibrium with glutamate, the labelling of [$^{13}$C]-glutamate in the C-4, 3 and 2 positions was observed. Since the flux of [$^{13}$C] labelled acetyl-CoA via the TCA cycle is orientation conserved, the labelling of [$^{13}$C]-glutamate is greater in the C-4, compared with the C-3 and C-2, positions. Thus, labelling was evaluated in the C-4 position of glutamate in COS/wtABAD versus COS/vector in cell lysates and supernatants. In culture supernatants, NMR data demonstrated greater labelling of the C-4 resonances in glutamate in COS/wtABAD cells, _2-fold, compared with COS/vector cells. Glutamine was not detected in supernatants from COS/wtABAD or COS/vector cells. The $^1$H NMR analysis of these supernatants revealed that the fractional enrichment at glutamate C-4 was 58±3% in COS/wtABAD transfectants compared with 41±2% in COS/vector cells. These data are indicative of increased metabolism of exogenous [$^{13}$C]-labelled β-hydroxybutyrate in COS cells overexpressing ABAD. In contrast, there were no observed differences between fractional enrichment at glutamate C-4 in cell lysates between COS/wtABAD and COS/vector cells, probably because glutamate is rapidly extruded into the medium (glutamine and glutamate levels in cell lysates were the same, comparing COS/wtABAD and COS/vector cells). The $^{13}$C and $^1$H NMR data demonstrate increased exogenous β-hydroxybutyrate utilization in the COS cells overexpressing wtABAD.

Upregulation of ABAD in response to cerebral ischemia. A severe form of metabolic stress is imposed by cerebral ischemia. Wild-type C57BL6 mice subjected to transient middle cerebral artery occlusion displayed increased levels of ABAD in neurons near the infarcted area, especially those in the penumbra, compared with the nonischemic hemisphere, using polyclonal antibody to recombinant mouse ABAD. Image analysis of multiple fields from sections similar to those shown in panels A-B demonstrated an _5-fold increase of ABAD antigen in cortical neurons consequent to stroke.

Characterization of Tg PD-ARAD mice. These data with wild-type mice subjected to cerebral ischemia suggested that upregulation of ABAD might be a component of the response to ischemic stress, and led us to make transgenic mice in which ABAD was overexpressed in cortical neurons. Three independent founders of Tg mice in which human ABAD is expressed under control of the human PDGF B-chain promoter have been identified and used to establish transgenic lines (at present backcrossed eight times into the C57BL6 background). Representative mice from each of these transgenic lines showed high levels of transgene activity at both the mRNA and protein levels in cerebral cortex. Immunoblotting performed on brain subregions from one line of Tg PD-ABAD mice, using an anti-human ABAD peptide antibody which selectively recognizes the human form of the protein, showed increased antigen especially in cerebral cortex and hippocampus, with a smaller increase in cerebellum. Immunohistochemical staining of ABAD in cerebral cortex confirmed high levels of antigen expression in cortical neurons compared with nontransgenic littermates. Semiquantitative analysis of immunohistochemical results using antibody reactive with murine and human ABAD antigen (i.e., total ABAD antigen) indicated that there was an _3.5–4-fold increase in total ABAD antigen in cerebral cortex comparing Tg mice with nonTg littermate control mice. Induction of stroke in transgenic mice further elevated ABAD antigen another two-fold compared with nonTg controls (24 hrs after the ischemic episode; not shown). Growth (height/weight) and reproductive fitness (number and size of litters) was similar between Tg PD-ABAD mice and nontransgenic (nonTg) controls, and there were no overt neurologic symptoms or other phenotype evident in these mice noted to date.

NMR analysis of $^{13}$C-β-hydroxybutyrate metabolism in Tg PD-ABAD mice. Tg PD-ABAD and control mice were infused with D-[2,4-$^{13}$C]-3-hydroxybutyrate. $^{13}$C NMR spectra of cerebral cortical extracts from Tg PD-ABAD and nonTg littermate control (the latter spectra are not shown) mice illustrate labelling of glutamate and glutamine in the C-4, C-3 and C-2 positions, as well as GABA in the C-2 position, consistent with entry of [$^{13}$C]-β-hydroxybutyrate via 2-[$^{13}$C]-acetyl-CoA into the TCA cycle. The intensity of glutamate and glutamine C-4 resonance was 50% and 20% greater, respectively, in Tg PD-ABAD mice compared with nonTg littermates. The glutamate to glutamine ratio, based on C-4 resonance area, was 3.6±0.3 in nonTg versus 2.1±0.4 in Tg PD-ABAD mouse brains (P<0.03). These data suggest that glutamine synthesis is more efficient in Tg PD-ABAD mouse brain compared with controls. The area of the $^{13}$C-labelled C-2 resonance of GABA was also greater in Tg PD-ABAD mice (4.8±0.3) than in nonTg controls (2.2±0.5; p<0.04). Such increased labelling of GABA is consistent with enhanced conversion of labelled glutamate to GABA in brains of Tg mice. $^1$H NMR analysis of these extracts revealed that the fractional enrichment in glutamate C-4 was significantly greater in Tg PD-ABAD (58±5%) than in nonTg littermates (38±7%; P<0.03). As might be expected from the increased utilization of exogenous β-hydroxybutyrate, measurement of basal ATP levels in cerebral cortex of Tg PD-ABAD mice fasted overnight showed a statistically significant increase compared with nonTg littermates. Similarly, levels of β-hydroxybutryate in the brains of Tg PD-ABAD mice were lower, compared with nonTg controls in view of its increased utilization in the presence of higher levels of neuronal ABAD.

Induction of stroke in Tg PD-ABAD mice. In order to assess the possible contribution of ABAD to ischemic stress, Tg PD-ABAD and age-matched nonTg littermate control mice were subjected to a 45 min period of transient middle cerebral artery occlusion followed by a 24 hr period for evolution of the cerebral infarct. These studies utilized a protocol which we have found to provide reproducible stroke volumes and functional data (neurologic deficit scores, cerebral blood flow)(45–48). Levels of ABAD increased an additional _2-fold in Tg PD-ABAD mice after stroke, versus with uninstrumented Tg PD-ABAD mice. Compared with nonTg littermate controls, Tg PD-ABAD mice displayed strokes of smaller volume and lower neurologic deficit scores (consistent with better maintenance of neurologic function). In contrast, there was no change in cerebral blood flow comparing the Tg and nonTg animals (not shown), consistent with a direct effect of ABAD on neurons, as ABAD was overexpressed in neurons by the PDGF B chain promoter. Analysis of cerebral cortex from Tg animals showed increased ATP and decreased lactate levels compared with nonTg controls. In addition, β-hydroxybutyrate levels were lower in animals subjected to cerebral ischemia, and this finding was much more pronounced in Tg PD-ABAD mice compared with nonTg littermate controls. These data are suggested better maintenance of energy reserve and substrate metabolism in Tg PD-ABAD mice subject to ischemia.

Discussion

ABAD is a member of the short-chain dehydrogenase/reductase family with remarkably broad substrate specificity, now extended to include the ketone body D-β-hydroxybutyrate. In comparison with mitochondrial D-β-hydroxybutyrate dehydrogenase (52–55), which displays $K_m$_1 mM, ABAD is similar with $K_m$_3.7 mM. At β-hydroxybutyrate concentrations in the plasma of normal individuals (<1 mM), both enzymes would be working considerably below their respective $K_m$'s. Under pathologic conditions, when β-hydroxybutyrate concentrations can reach the millimolar range (21–23), both enzymes would be expected to metabolize β-hydroxybutyrate. However, the maximal activity of ABAD (0.0037_mole/min/mg) is much lower than that for the mitochondrial enzyme, $V_{max}$_100–175_moles/min/mg protein with β-hydroxybutyrate (54,55). D-β-hydroxybutyrate dehydrogenase is a housekeeping metabolic enzyme present in mitochondria whose expression has not been reported to vary in pathologic states, beyond its loss from severely ischemic cardiac tissue (56–57). ABAD, present in both endoplasmic reticulum and mitochondria, displays a pattern of expression sensitive to environmental perturbations, including increased expression in brains of patient's with Alzheimer's disease (13) and at sites of ischemic brain injury. Thus, in settings where ABAD expression is enhanced, the enzyme could, potentially, contribute to the metabolism of β-hydroxybutyrate. However, the situation is likely to be more complex in vivo, since Tg PD-ABAD mice display increased flux of acetyl-CoA through the TCA cycle and higher ATP levels in the cerebral cortex, even though the level of ABAD expression is only increased by about 3.5–4-fold, compared with nontransgenic controls. These data indicate that ABAD clearly has the potential to contribute to β-hydroxybutyrate metabolism, though the extent of its contribution is likely to depend on the particular situation.

Increased expression of ABAD in human brain following cerebral infarction and in response to experimentally-induced cerebral ischemia suggests that induction of ABAD might subserve normal protective mechanisms. In view of the complexities of cellular metabolic pathways, it was necessary to prove that ABAD could promote metabolic homeostasis in response to nutritional deprivation. ABAD-transfected COS cells displayed increased energy charge and flux of acetyl-CoA through the TCA cycle in medium containing β-hydroxybutyrate compared with controls in which the active site of ABAD was mutationally inactivated. Enhanced metabolic homeostasis was reflected by maintenance of MTT reduction and morphologic phenotype in ABAD-transfected COS cells. Similarly, transgenic mice overexpressing ABAD in cortical neurons demonstrated increased flux of acetyl-CoA through the TCA cycle following β-hydroxybutyrate infusion compared with nontransgenic littermates. However, increased basal levels of ATP (and energy charge; data not shown) in brains of Tg PD-ABAD mice, even before nutritional stress, was unexpected, and suggests a more general protective potential of ABAD in response to a range of environmental challenges. This apparent increase in the overall energy charge in the presence of ABAD, implies that the enzyme may render neurons metabolically more stable and, thus, less susceptible to fluctuations in substrate availability.

A decreased lactate content in the cerebral cortex of Tg PD-ABAD mice subjected to stroke suggests two important events associated with neuroprotection. First, decreased tissue lactate and lower lactate/pyruvate ratio in the Tg PD-ABAD mice are indicative of diminished cytosolic NADH/NAD$^+$ ratio and consistent with decreased reductive stress. In this context, studies have suggested that diminished in reductive stress may translate into lower reactive oxygen species generation upon reperfusion (58). Second, decreased tissue lactate is also indicative of efficient lactate efflux in stroke-prone tissue thereby alleviating feedback inhibition brought about by metabolic intermediates of glycolysis (59–61).

Our NMR measurements were based on conversion of α-ketoglutarate, an intermediate in the TCA cycle, to glutamate. However, we also observed conversion of glutamate, thus formed, to glutamine and GABA. These data indicate that ketone bodies, such as β-hydroxybutyrate, can provide both a substrate for maintenance for cellular energy charge, as well as a source for increased production of neurotransmitters. To our knowledge, this is the first time that the conversion of labelled β-hydroxybutyrate to GABA and glutamate has been demonstrated in vivo. Furthermore, the increased production of $^{13}$C-labelled GABA and glutamate from [$^{13}$C]-β-hydroxybutyrate in Tg PD-ABAD mice, compared with controls, indicates that ABAD provides a novel means for sustaining energy production and replenishing neurotransmitters in the brain using ketone bodies as the substrate. At this point, it is unclear whether neuroprotection afforded by overexpression of ABAD is due solely to its effect on ATP levels and/or changes in neurotransmitter metabolism.

In contrast to this cytoprotective facet of ABAD biology, we have proposed that in the presence of Aβ, another, quite different, aspect of ABAD's properties becomes manifest (14). In an Aβ-rich environment, ABAD generates reactive oxygen intermediates and toxic reactive aldehydes based on cotransfection experiments using cultured Cos and neuroblastoma cells(14)(unpublished observation)[2]. Furthermore, pilot studies with double transgenic mice, resulting from a cross of Tg PD-ABAD mice with transgenic mice overexpressing mutant βAPP, have shown accelerated expression of cell stress markers (4-hydroxynonenal and heme oxygenase type 1), compared with single transgenic mice, and nontransgenic controls[2]. Based on these data, ABAD appears to have chameleon-like properties depending on the local environment, in particular related to the presence of Aβ. Our future studies have the goal of determining how ABAD's properties become modulated in an Aβ-rich environment, and whether this translates into accelerated and more severe neuronal dysfunction/toxicity. The current studies provide a foundation for evaluating metabolic properties of ABAD in response to cellular stress in vitro and in vivo.

Reference for Example 4

1. Hardy, J. (1997) *TrendsNeurosci.* 296, 28570–26998
2. Citron, M., Westaway, D., Xia, W., Carlson, G., Diehl, T., Levesque, G., Johnson-Wood, K., Lee, M., Seubert, P., Davis, A., Kholodenko, D., Motter, R., Sherrington, R., Perry, B., Yao, H., Strome, R., Lieberburg, I., Rommens, J., Kim, S., Schenk, D., Fraser, P., St. George-Hyslop, P., and Selkoe, D. (1997) *NatureMed.* 3, 67–72
3. St. George-Hyslop, P (1998) *Neurobiol. Aging* 19, 133–137
4. Selkoe, D. (1999) *Ann. Rev. Cell Biol.* 10, 373–403
5. Liao, A., Nitsch, R., Greenberg, S., Finckh, U., Blacker, D., Albert, M., Rebeck, G., Gomez-Isla, T., Clatworthy, A., Binetti, G., Hock, C., Mueller-Thomsen, T., Mann, U., Zuchowski, K., Beisiegel, U., Staehelin, H., Growdon, J., Tanzi, R., and Hyman, B. (1998) *Human Molec. Gen.* 12, 1953–1956
6. Kisilevsky, R., Lemieux, J., Fraser, P., Kong, X., Hultin, P., and Szarek, W. (1995) *Nature Med.* 1, 143–148
7. Goldgaber, D., Schwarzman, A., Bhasin, R., Gregori, L., Schmechel, D., Saunders, A. M., Roses, A. D., and Strittmatter, W. J. (1993) *Annals New York Acad. Sci.* 695, 139–143
8. Roses, A. (1998) *Ann. New York Acad. Sci.* 855, 738–743
9. Hensley, K., Carney, J., Mattson, M., Aksenova, M., Harris, M., Wu, J., Floyd, R., and Butterfield, D. (1994) *Proc. Natl. Acad. Sci. (U.S.A.)* 91, 3270–3274
10. Mattson, M. and Goodman, Y. (1995) *Brain Res.* 676, 219–224
11. Mark, R., Blanc, E., and Mattson, M. (1996) *Mol. Neurobiol.* 12, 915–924
12. Mattson, M. (1995) *Neurobiol. Aging* 16, 679–682
13. Yan, S. D., Fu, J., Soto, C., Chen, X., Zhu, H., Al-Mohanna, F., Collison, K., Zhu, A., Stern, E., Saido, T., Tohyama, M., Ogawa, S., Roher, A., and Stern, D. (1997) *Nature(Lond.)* 389, 689–695
14. Yan, S-D., Shi, Y., Zhu, A., Fu, J., Zhu, H., Zhu, Y., Gibson, L., Collison, K., Al-Mohanna, F., Ogawa, S., Roher, A., Clarke, S., and Stern, D. M. (1998) *J. Biol. Chem.* 274, 2145–2156
15. Jornvall, H., Persson, B., Krook, M., Atrian, S., Duarte-Gonzalez, R., Jeffer, J., and Ghosh, D. (1995) *Biochemistry* 34, 6003–6013
16. Furuta, S., Kobayashi, A., Miyazawa, S., and Hashimoto, T. (1997) *Biochim. Biophys. Acta.* 1350, 317–324
17. Kobayashi, A., Jiang, L., and Hashimoto, T. (1996) *J. Biochem.* 119, 775–782
18. He, X-Y., Schulz, H., and Yang, S-Y. (1998) *J. Biol. Chem.* 273, 10741–10746
19. He, X-Y., Merz, G. , Mehta, P., Schulz, H., and Yang, S-Y. (1999) *J. Biol. Chem.* 274, 15014–15019
20. Torroja, L., Ortuno-Sahagun, D., Ferrus, A., Hammerle, B., and Barbas, J. (1998) *J. Cell. Biol.* 141, 1009–1017
21. Levitsky, L., Fisher, D., Paton, J., and Delannoy, C. (1977) *Pediatr. Res.* 11, 298–302
22. Owen, O., Morgan, A., Kemp, H., Sullivan, J., Herrera, M., and Cahill. G. (1967) *J. Clin. Invest.* 46, 1589–1595
23. Petersson, B., Settergren, G., and Dahlquist, G. (1972) *Acta Paediat. Scand.* 61, 273–277
24. Segel, I. H. (1975) *Enzyme Kinetics, Behavior, and Analysis of Rapid Equilibrium and Steady-State Enzyme Systems*, Wiley-Interscience, New York
25. Johnson, D., Gautsch, J., Sportsman, J., and Elder, J. (1984) *Gene Anal. Tech.* 1, 3–8
26. Schmidt, A. M., Vianna, M., Gerlach, M., Brett, J., Ryan, J., Kao, J., Esposito, C., Hegarty, H., Hurley, W., Clauss, M., Wang, F., Pan, Y. C., Tsang, T. C., and Stern, D. M. (1992) *J. Biol. Chem.* 267, 14987–14997
27. Schmidt, A. M., Hori, O., Brett, J., Yan, S. D., Wautier, J. L., and Stern, D. M. (1994) *Arterioscler. Thromb.* 14, 1521–1528
28. Kuwabara, K., Matsumoto, M., Ikeda, J., Ogawa, S., Maeda, Y., Kitagawa, K., Imuta, N., Kinoshita, T., Stern, D., Yangi, H., and Kamada, T. (1996) *J. Biol. Chem.* 271, 5025–5032
29. Du, Y., Dodel, R., Bales, K., Jemmerson, R., Hamilton-Byrd, E., and Paul, S. (1997) *J. Neurochem.* 69, 1382–1388
30. Sonnewald, U., Westergaard, N. Hassel, B., Muller, T., Unsgard, G., Fonnum, F., Hertz, L., Schousboe, A., and Petersen, S. (1993) *Dev. Neurosci.* 15, 351–358
31. Badar-Goffer, R., Bachelard, H., and Morris, P. (1990) *Biochem. J.* 266, 133–139
32. Jones, J., Hansen, J., Sherry, A., Malloy, C., and Victor, R. (1997) *Analytical Biochemistry* 249, 201–206
33. London, R. (1988) *Prog. NMR Spectroscopy* 20, 337–383
34. Malloy, C., Sherry, A., and Jeffrey, F. (1987) *FEBS Lett.* 212, 58–62
35. Trueblood, N. and Ramasamy, R. (1998) *Am. J. Physiol.* 275, H75–H83
36. Chatham, J., Forder, J., Glickson, J., and Chance, E. (1995) *J. Biol. Chem.* 270, 7999–8008
37. Jeffrey, F., Diczku, V., Sherry, A., and Malloy, C. (1995) *Basic Res. Cardiol.* 90, 388–396
38. Fitzpatrick, S., Hetherington, H., Behar, K., and Shulman, R. (1990) *J. Cereb. Blood Flow and Metab.* 10, 170–179
39. Behl, C., Davis, J., Lesley, R., and Schubert, D. (1994) *Cell* 77, 817–827
40. Imuta, N., Ogawa, S., Maeda, Y., Kuwabara, K., Hori, O., Ueda, H., Tanagihara, T., and Tohyama, M. (1998) *J. Neurochem.* 70, 550–557
41. Ueda, H., Hashimoto, T., Furuya, E., Tagawa, K., Kitagawa, K., Matsumoto, M., Yoneda, S., Kimura, K., and Kamada, T. (1988) *J. Biochem.* (Tokyo) 104, 81–86
42. Sasahara, M., Fries, J., Raines, E., Gown, A., Westrum, L., Frosch, M., Bonthron, D., Ross, R., and Collins, T. (1991) *Cell* 64, 217–227
43. Kang, D., Soriano, S., Frosch, M., Collins, T., Naruse, S., Sisodia, S., and Koo, E. (1999) *J. Neurosci.* 19, 4229–4237
44. Berezovska, O., Frosch, M., McLean, P. Knowles, R., Koo, E., Kang, D., Lu, F., Lux, S., Shen, J., onegawa, S., Hyman, B., (1999) *Brain Res. Mol. Brain Res.* 69, 273–280

45. Huang, J., Kim, L., Mealey, R., March, H., Zhang, A., Tenner, E., Connolly, E., and Pinsky, D. (1999) *Science* 285, 595–599
46. Connolly, E. S., Winfree, C. J., Stern, D. M., Solomon, R. A., and Pinsky, D. J. (1996) *Neurosurg.* 38, 523–532
47. Connolly, E., Winfree, C., Springer, T., Naka, Y., Liao, H., Yan, S-D., Stern, D., Solomon, R., Gutierrez-Ramos, J-C., and Pinsky, D. (1996) *J. Clin. Invest.* 97, 209–216
48. Connolly, E., Winfree, C., Prestigiacomo, C., Kim, S., Choudhri, T., Hoh, B., Naka, Y., Solomon, R., and Pinsky, D. (1997) *Circ. Res.* 81, 304–310
49. Bederson, J. B., Pitts, L. H., and Tsuji, M. (1986) *Stroke* 17, 472–476
50. Sellevold, O., Jynge, P., and Aarstad, K. (1986) *J. Mol. Cell. Cardiol.* 18, 517–527
51. Lamprecht, W. and Heinz, F. (1995) *Method of Enzymatic Analysis*, Verlag Chemie, Boca Raton, Fla.
52. McCann, W. (1957) *J. Biol. Chem.* 226, 15–22
53. Lehninger, A., Sudduth, H., and Wise, J. (1960) *J. Biol. Chem.* 235, 2450–2455
54. Bock, H., and Fleischer, S. (1975) *J. Biol. Chem.* 250, 5774–5781
55. McIntyre, J., Latruffe, N., Brenner, S., and Fleischer, S. (1988) *Arch. Biochem. Biophys.* 262, 85–98
56. Evertsen, F., Medbo,J., Jebens, E., and Gjovaag, T. (1999) *Acta Physiol. Scanda* 167, 247–257
57. Frederiks, W., Tukkie, R., Grundeman, P., Schellens, J. (1995) *J. Pathol.* 175, 339–348
58. Williamson, J., Chang, K., Frangos, M., Hasan, K., Ido, Y., Kawamura, T., Nyengaard, J., Van den Enden, M., Kilo, C., and Tilton, R. (1993) *Diabetes* 42, 801–813
59. Neely, J. and Morgan, H. (1974) *Ann. Rev. Physiol.* 36, 413–459
60. King, L. and Opie, L. (1998) *Mol. Cell. Biochem.* 180, 3–26
61. Lipton, P. (1999) *Physiol. Rev.* 79, 1431–1568

The following description of figures are provided as descriptions of the results from Example 4. There are no pictures/illustrations/drawings submitted to correspond to these descriptions.

Summary

Amyloid β-peptide Binding Alcohol Dehydrogenase (ABAD) is a member of the family of short-chain dehydrogenase/reductases whose distinctive properties include the capacity to bind amyloid beta-peptide (Aβ) and enzymatic activity towards a broad array of substrates. In view of ABAD's properties as a 3-hydroxyacyl-CoA dehydrogenase, the hypothesis was tested that this enzyme would promote the cellular response to nutritional deprivation when ketone bodies are important energetic substrates. This hypothesis has proven to be correct based on experimental evidence from in vitro and in vivo studies presented in this manuscript. Stably-transfected COS cells overexpressing ABAD incubated in with medium devoid of glucose, and supplemented with β-hydroxybutyrate and dialyzed serum displayed enhanced metabolic homeostasis compared with vector-transfected COS cells (maintenance of energy charge, MTT reduction and morphologic phenotype). In addition, we have made transgenic mice overexpressing ABAD under control of the platelet-derived growth factor B chain promoter (Tg PD-ABAD) which are shown to have high levels of ABAD in cortical neurons. Consistent with our in vitro results, transient middle cerebral artery occlusion (a severe model of nutritional deprivation) in Tg PD-ABAD mice resulted in strokes of smaller volume and lower neurologic deficit scores compared with nontransgenic littermate controls. Tg mice also showed increased flux of acetyl-CoA through the TCA cycle, as well as increased labelling of glycogen and elevated ATP levels in cerebral cortex compared with nontransgenic controls. These data suggest that ABAD contributes to the protective response to metabolic stress, especially in the setting of ischemia.

Referecnces for Example

1. Yan SD, Fu J, Soto C, Chen X, Zhu H, Al-Mohanna F, Collison K, Zhu A, Stern E, Saido T, Tohyama M, Ogawa S, Roher A, Stern D: An intracellular protein that bind amyloid-beta peptide and mediates neurotoxicity in Alzheimer's disease. *Nature*(Lond) 1997;389:689–695
2. Yan S-D, Shi Y, Zhu A, Fu J, Zhu H, Zhu Y, Gibson L, Collison K, Al-Mohanna F, Ogawa S, Roher A, Clarke S, Stern DM: Role of ERAB/L-3-hydroxyacyl-Coenzyme A dehydrogenase type II activity in amyloid beta-peptide-induced cytotoxicity. *J Biol Chem* 1998;274:2145–2156
3. Furuta S, Kobayashi A, Miyazawa S, Hashimoto T: Cloning and expression of cDNA for a newly identified iszyme of bovine liver 3-hydroxyacyl-CoA dehydrogenase and its import into mitochondria. *Biochim Biophys Acta* 1997;1350:317–324
4. Kobayashi A, Jiang L, Hashimoto T: Two mitochondrial 3-hydroxyacyl-CoA dehydrogenases in bovine liver. *J Biochem* 1996;119:775–782
5. He X-Y, Schulz H, Yang S-Y: A human brain L-3-hydroxyacyl-coenzyme A dehydrogenase is identical to amyloid beta-peptide-binding protein involved in Alzheimer's disease. *J Biol Chem* 1998;273:10741–10746
6. He X-Y, Merz.G, Mehta P, Schulz H, Yang S-Y: Human brain short chain L-3-hydroxyacyl Coenzyme A dehydrogenase is a single-domain multifunctional enzyme. *J Biol Chem* 1999;274:15014–15019
7. Torroja L, Ortuno-Sahagun D, Ferrus A, Hammerle B, Barbas J: scully, an essential gene of Drosophila, is homologous to mammalian mitochondrial type II L-3-hydroxygacyl-CoA dehydrogenase/Amyloid-beta petide-binding protein. *J Cell Biol* 1998;141:1009–1017
8. Sasahara M, Fries J, Raines E, Gown A, Westrum L, Frosch M, Bonthron D, Ross R, Collins T: PDGF B-chain in neurons of the central nervous system, posterior pituitary and in a transgenic model. *Cell* 1991;64:217–227
9. Kang D, Saitoh T, Chen X, Xia Y, Maslian E, Hansen L, Thomas R, Thal L, Katzman R: Genetic assocation of LRP with late-onset Alzheimer's disease. *Neurology* 1997;49:56–61
10. Berezovska O, Frosch M, McLean P, Knowles R, Koo E, Kang D, Shen J, Lu F, Lux S, Tonegawa S, Hyman B: The Alzheimer-related gene presenilin 1 facilitates notch 1 in primary mammalian neurons. *Molec Brain Res* 1999;69:273–280
11. Laemmli U: Cleavage of structural proteins during the assembly of the head of bacteriophage T4. *Nature* 1970;227:680–685
12. Yan S-D, Chen X, Chen M, Zhu H, Roher A, Slattery T, Zhao L, Nagashima M, Morser J, Migheli A, Nawroth P, Stern D M, Schmidt A-M: RAGE and amyloid-beta peptide neurotoxicity in Alzheimer's disease. *Nature* 1996;382:685–691
13. Yan S-D, Zhu H, Zhu A, Golabek A, Roher A, Yu J, Soto C, Schmidt A-M, Stern D M, Kindy M: Receptor-dependent cell stress and amyloid accumulation in systemic amyloidosis. *Nat Med* 2000;6:643–651
14. Hsia A, Masliah E, McConlogue L, Yu G-Q, Tatsuno G, Hu K, Kholodenko D, Malenka R, Nicoll R, Mucke L: Plaque-independent disruption of neural circuits in Alzheimer's disease mouse models. *Proc Natl Acad Sci (USA)* 1999;96:3228–3233

15. Terry R, Masliah E, Salmon D, Butters N, DeTeresa R, Hill R, Hansen L, Katzman R: Physical basis of cognitive alterations in Alzheimer disease: synapse loss is the major correlate of cognitive impairment. *Ann Neurol* 1991;30:572–580

16. Zhan S, Beyreuther K, Schmitt H: Quantitative assessment of synaptophysin immunoreactivity of the corticla neuropil in various neurodegenerative diseases with dementia. *Dementia* 1993;4:66–74

17. Dickson D, Crystal H, Bevona C, Honer W, Vincent I, Davies P: Correlation of synaptic and pathological markers incognition in the elderly. *Neurobiol Aging* 1995;16:285–304

18. Sze C, Troncoso J, Kowas C, Mouton P, Price D, Martin J: Loss of presynaptic vesicle protein synaptophysin in hippocampus correlates with cognitive decline in Alzheimer disease. *J Neuropathol Exp Neurol* 1997;56:933–944

19. Samuel W, Alford M, Hofstetter C, Hansen L: Dementia with Lewy bodies versus pure Alzheimer disease: differences in cognition, neuropathology, cholinergic dysfunction, and synapse density. *J Neuropathol Exp Neurol* 1997;56:499–508

20. Brown D, Risser R, Bigio E, Tripp P, Stiegler A, Welch E, Eagan K, Hladik C, White C: Neocortical synatpic density and Braak stage in Lewy body variant of Alzheimer disease. *J Neuropathol Exp Neurol* 1998;58:955–960

21. Masliah E, Achim C, Ge N, DeTeresa R, Terry R, Wiley C: The spectrum of human immunodeficiency virus-associated neocortical damage. *Ann Neurol* 1992;32:321–329

22. Yan S-F, Tritto I, Pinsky D J, Liao H, May L, Stern D M: Induction of interleukin 6 (IL-6) by hypoxia in vascular cells: central role of the binding site for nuclear. factor-IL-6. *J Biol Chem* 1995;270:11463–11471

23. Dignam J, Lebovitz R, Roeder R: Accurate transcription initiation by RNA polymerase II in a soluble extract from isolated mammalian nuclei. *Nucl Acids Res* 1983;11:1475–1489

24. White A, Zheng H, Galatis D, Maher F, Hesse L, Multhaup G, Beyreuther K, Masters C, Cappai R: Survival of cultured neurons from amyloid precursor protein knock-out mice against Alzheimer's amyloid-β toxicity and oxidative stress. *J Neurosci* 1998;18:6207–6217

25. Jones J, Hansen J, Sherry A, Malloy C, Victor R: Determination of acetyl-CoA enrichment in rat heart and skeletal muscle by 1H nuclear magnetic resonance analysis of glutamate in tissue extracts. *Analytical Biochemistry* 1997;249:201–206

26. London R: 13C labelling in studies of metabolic regulation. *Prog NMR Spectroscopy* 1988;20:337–383

27. Malloy C, Sherry A, Jeffrey F: Carbon flux through citric acid cycle pathways in perfused heart by 13C NMR spectroscopy. *FEBS Lett* 1987;212:58–62

28. Trueblood N, Ramasamy R: Aldose reductase inhibition improves altered glucose metabolism of isolated diabetic rat hearts. *Am J Physiol* 1998;275:H75–H83

29. Chatham J, Forder J, Glickson J, Chance E: Calculation of absolute metabolic flux and the elucidation of the pathways of glutamate labelling in perfused rat heart by 13C NMR spectroscopy and nonlinear least squares analysis. *J Biol Chem* 1995;270:7999–8008

30. Jeffrey F, Diczku V, Sherry A, Malloy C: Substrate selection in the isolated working rat heart: effects of reperfusion, afterload, and concentration. *Basic Res Cardiol* 1995;90:388–396

31. Fitzpatrick S, Hetherington H, Behar K, Shulman R: Flux from glucose to glutamate in the rat brain in vivo as determined by 1H-observed, 13C-edited NMR spectroscopy. *J Cereb Blood Flow and Metab* 1990;10:170–179

32. Huang J, Kim L, Mealey R, March H, Zhang A, Tenner E, Connolly E, Pinsky D: Neuronal protection in stroke by an sLex-glycosylated complemetn inhibitory protein. *Science* 1999;285:595–599

33. Connolly E S, Winfree C J, Stern D M, Solomon R A, Pinsky D J: Procedural and strain-related variables significantly affect outcome in a murine model of focal cerebral ischemia. *Neurosurg* 1996;38:523–532

34. Connolly E S J, Winfree C J, Springer T A, Naka Y, Liao H, Yan S D, Stern D M, Solomon R A, Gutierrez-Ramos J-C, Pinsky D J: Cerebral protection in homozygous null ICAM-1 mice after middle cerebral artery occlusion. Role of neutrophil adhesion in the pathogenesis of stroke. *J Clin Invest* 1996;97:209–216

35. Connolly E, Winfree C, Prestigiacomo C, Kim S, Choudhri T, Hoh B, Naka Y, Solomon R, Pinsky D: Exacerbation of cerebral injury in mice with express the P-selectin gene: identification of P-selectin blockade as a new target for treatment of stroke. *Circ Res* 1997;81:304–310

36. Bederson J B, Pitts L H, Tsuji M: Rat middle cerebral artery occlusion: evaluation of the model and development of a neurologic examination. *Stroke* 1986;17:472–476

---

What is claimed is:

1. A transgenic mouse whose genome comprises a recombinant DNA sequence comprising a nerve tissue-specific promoter operatively linked to a DNA sequence encoding amyloid-beta peptide alcohol dehydrogenase (ABAD), wherein said transgenic mouse overexpresses ABAD in the brain and, relative to a non-transgenic littermate, exhibits at least one phenotype selected from (i) an elevated level of basal ATP and (ii) protection from metabolic or ischemic stress.

2. The transgenic mouse of claim 1, wherein protection from ischemic stress comprises a decrease in infarct volume or lower neurologic deficit scores in response to ischemic injury relative to a non-transgenic littermate.

3. The transgenic mouse of claim 1, wherein the promoter is platelet derived growth factor (PDGF)-B-chain promoter.

4. A method for evaluating in a transgenic mouse the potential therapeutic effect of a compound for treating pathogenesis of Alzheimer's disease in a human, which comprises:
   (a) administering the compound to a transgenic mouse whose genome comprises a recombinant DNA sequence comprising a nerve tissue-specific promoter operatively. linked to a DNA sequence which encodes amyloid-beta peptide alcohol dehydrogenase (ABAD), wherein said mouse overexpresses ABAD in the brain and, relative to a non-transgenic littermate, exhibits at least one phenotype selected from the group consisting of (i) an elevated level of basal ATP in cerebral cortex, (ii) a decreased lactate level in cerebral cortex which has been subjected to cerebral ischemia, (iii) more efficient glutamine synthesis, and (iv) a lower beta-hydroxybutyrate level in cerebral cortex which has been subjected to cerebral ischemia; and
   (b) determining the therapeutic effect of the compound on the transgenic mouse by monitoring basal synaptic transmission or synaptic plasticity or basal levels of ATP, wherein an increase in basal synaptic transmission or synaptic plasticity or basal levels of ATP indicates that the compound would have a potential therapeutic effect on pathogenesis of Alzheimer's disease in a human.

5. The method of claim 4, wherein the promoter is platelet derived growth factor (PDGF)-B-chain promoter.

6. A transgenic mouse whose genome comprises a recombinant,DNA sequence comprising:
   (a) a nerve tissue-specific promoter; and
   (b) a DNA sequence which encodes amyloid-beta peptide alcohol dehydrogenase (ABAD),
   wherein the promoter and the DNA sequence which encodes amyloid-beta peptide alcohol dehydrogenase are operatively linked to each other and integrated in the genome of the mouse, and
   wherein said mouse overexpresses ABAD in the brain and, relative to a non-transgenic littermate, exhibits at least one phenotype selected from the group consisting of (i) an elevated level of basal ATP in cerebral cortex, (ii) decreased lactate level in cerebral cortex which has been subjected to cerebral ischemia, (iii) more efficient glutamine synthesis, and (iv) lower beta-hydroxybutyrate level in cerebral cortex which has been subjected to cerebral ischemia.

7. The transgenic mouse of claim 6, wherein the promoter is platelet derived growth factor (PDGF)-B-chain promoter.

8. The transgenic mouse of claim 6, wherein the DNA sequence which encodes amyloid-beta peptide alcohol dehydrogenase is a human DNA sequence.

* * * * *

SEQUENCE LISTING

```
<160> NUMBER OF SEQ ID NOS: 7

<210> SEQ ID NO 1
<211> LENGTH: 21
<212> TYPE: PRT
<213> ORGANISM: Rat

<400> SEQUENCE: 1

Ile Glu Asn Pro Phe Leu Asn Gly Glu Val Ile Arg Leu Asp Gly Ala
 1               5                   10                  15

Ile Arg Met Gln Pro
            20
```

-continued

<210> SEQ ID NO 2
<211> LENGTH: 261
<212> TYPE: PRT
<213> ORGANISM: Human

<400> SEQUENCE: 2

Met Ala Ala Ala Cys Arg Ser Val Lys Gly Leu Val Ala Val Ile Thr
1               5                   10                  15

Gly Gly Ala Ser Gly Leu Gly Leu Ala Thr Ala Glu Arg Leu Val Gly
            20                  25                  30

Gln Gly Ala Ser Ala Val Leu Leu Asp Leu Pro Asn Ser Gly Gly Glu
        35                  40                  45

Ala Gln Ala Lys Lys Leu Gly Asn Asn Cys Val Phe Ala Pro Ala Asp
    50                  55                  60

Val Thr Ser Glu Lys Asp Val Gln Thr Ala Leu Ala Leu Ala Lys Gly
65                  70                  75                  80

Lys Phe Gly Arg Val Asp Val Ala Val Asn Cys Ala Gly Ile Ala Val
                85                  90                  95

Ala Ser Lys Thr Tyr Asn Leu Lys Lys Gly Gln Thr His Thr Leu Glu
            100                 105                 110

Asp Phe Gln Arg Val Leu Asp Val Asn Leu Met Gly Thr Phe Asn Val
        115                 120                 125

Ile Arg Leu Val Ala Gly Glu Met Gly Gln Asn Glu Pro Asp Gln Gly
    130                 135                 140

Gly Gln Arg Gly Val Ile Ile Asn Thr Ala Ser Val Ala Ala Phe Glu
145                 150                 155                 160

Gly Gln Val Gly Gln Ala Ala Tyr Ser Ala Ser Lys Gly Gly Ile Val
                165                 170                 175

Gly Met Thr Leu Pro Ile Ala Arg Asp Leu Ala Pro Ile Gly Ile Arg
            180                 185                 190

Val Met Thr Ile Ala Pro Gly Leu Phe Gly Thr Pro Leu Leu Thr Ser
        195                 200                 205

Leu Pro Glu Lys Val Cys Asn Phe Leu Ala Ser Gln Val Pro Phe Pro
    210                 215                 220

Ser Arg Leu Gly Asp Pro Ala Glu Tyr Ala His Leu Val Gln Ala Ile
225                 230                 235                 240

Ile Glu Asn Pro Phe Leu Asn Gly Glu Val Ile Arg Leu Asp Gly Ala
                245                 250                 255

Ile Arg Met Gln Pro
            260

<210> SEQ ID NO 3
<211> LENGTH: 973
<212> TYPE: DNA
<213> ORGANISM: Human

<400> SEQUENCE: 3
tcccgtggag tggccggcga caagatggca gcagcgtgtc ggagcgtgaa gggcctggtg      60
gcggtaataa ccggaggagc ctcgggcctg gcctggcca cggcggagcg acttgtgggg     120
cagggagcct ctgctgtgct tctggacctg cccaactcgg gtggggaggc ccaagccaag     180
aagttaggaa acaactgcgt tttcgcccca gccgacgtga cctctgagaa ggatgtgcaa     240
acagctctgg ctctagcaaa aggaaagttt ggccgtgtgg atgtagctgt caactgtgca     300
ggcatcgcgg tggctagcaa gacgtacaac ttaaagaagg ccagaccca taccttggaa     360

```
gacttccagc gagttcttga tgtgaatctc atgggcacct tcaatgtgat ccgcctggtg     420
gctggtgaga tgggccagaa tgaaccagac cagggaggcc aacgtggggt catcatcaac     480
actgccagtg tggctgcctt cgagggtcag gttggacaag ctgcatactc tgcttccaag     540 ggggaatag tgggcatgac actgcccatt gctcgggatc tggctcccat aggtatccgg      600
gtgatgacca ttgccccagg tctgtttggc accccactgc tgaccagcct cccagagaaa     660
gtgtgcaact tcttggccag ccaagtgccc ttccctagcc gactgggtga ccctgctgag     720
tatgctcacc tcgtacaggc catcatcgag aacccattcc tcaatggaga ggtcatccgg     780
ctggatgggg ccattcgtat gcagccttga agggagaagg cagagaaaac acacgctcct     840
ctgcccttcc tttccctggg gtactactct ccagtcttgg gaggaagccc agtagccatt     900
ttgtaactgc ctaccagtcg ccctctgtgc ctaataaagt ctcttttcct cacagaaaaa     960
aaaaaaaaaa aaa                                                        973
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR
      Primers

<400> SEQUENCE: 4

```
ggcagcagcg tgtcggagcg                                                  20
```

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: PCR
      Primers

<400> SEQUENCE: 5

```
agggcagagg agcgtgtgt                                                   19
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: PCR
      Primers

<400> SEQUENCE: 6

```
gacaagtatc tcgagacacc tggggatgag                                       30
```

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: PCR
      Primers

<400> SEQUENCE: 7

```
aaagaacttg taggttggat tttcgtacc                                        29
```